(12) United States Patent
Koga

(10) Patent No.: US 11,436,920 B2
(45) Date of Patent: Sep. 6, 2022

(54) SYSTEM FOR ESTIMATING POTENTIAL RISK AREA WHEN VEHICLE IS TRAVELING

(71) Applicant: HONDA MOTOR CO., LTD., Tokyo (JP)

(72) Inventor: Futoshi Koga, Wako (JP)

(73) Assignee: HONDA MOTOR CO., LTD., Tokyo (JP)

(*) Notice: Subject to any disclaimer, the term of this patent is extended or adjusted under 35 U.S.C. 154(b) by 0 days.

(21) Appl. No.: 17/196,583

(22) Filed: Mar. 9, 2021

(65) Prior Publication Data

US 2021/0192942 A1     Jun. 24, 2021

Related U.S. Application Data

(63) Continuation of application No. PCT/JP2018/036363, filed on Sep. 28, 2018.

(51) Int. Cl.
*G08G 1/01* (2006.01)
*G01C 21/36* (2006.01)

(52) U.S. Cl.
CPC ......... *G08G 1/0137* (2013.01); *G08G 1/0112* (2013.01); *G01C 21/3697* (2013.01)

(58) Field of Classification Search
CPC . G08G 1/0137; G08G 1/0112; G01C 21/3697
See application file for complete search history.

(56) References Cited

U.S. PATENT DOCUMENTS

| 6,870,478 B2 | 3/2005 | Yasushi et al. |
| 2015/0179073 A1* | 6/2015 | Suzuno ............... A61B 5/18 |
| | | 701/45 |
| 2016/0253895 A1* | 9/2016 | Prakah-Asante ...... G16H 40/67 |
| | | 340/539.12 |

(Continued)

FOREIGN PATENT DOCUMENTS

| JP | 4514372 B2 | 7/2010 |
| JP | 2013-205965 A | 10/2013 |
| JP | 2018-45303 A | 3/2018 |

(Continued)

OTHER PUBLICATIONS

International Search Report w/English translation and Written Opinion in Japanese dated Dec. 25, 2018, issued in counterpart International Application No. PCT/JP2018/036363 (9 pages).

(Continued)

*Primary Examiner* — Hongmin Fan
(74) *Attorney, Agent, or Firm* — WHDA, LLP

(57) ABSTRACT

An information providing system for reducing the processing load when estimating a potential risk area when a vehicle is traveling is provided. The information providing system acquires heart rate data of an occupant of the vehicle acquired by a wearable terminal attached to the occupant. The information providing system estimates a potential risk area that is a cause to increase a heart rate based on the heart rate data acquired. The information providing system specifies a point in time a predetermined time before a point in time at which the heart rate indicated by the heart rate data increases, and estimates the position of the vehicle corresponding to the specified point in time as the potential risk area.

15 Claims, 16 Drawing Sheets

(56) References Cited

U.S. PATENT DOCUMENTS

2017/0151957 A1\* 6/2017 Boesen .............. A61B 5/14532
2018/0194280 A1\* 7/2018 Shibata .............. G01C 21/3484

FOREIGN PATENT DOCUMENTS

| JP | 6301758 B2 | 3/2018 |
| --- | --- | --- |
| WO | 2007/114015 A1 | 10/2007 |
| WO | 2009/128398 A1 | 10/2009 |

OTHER PUBLICATIONS

International Preliminary Report on Patentability (Form PCT/IPEA/409) of International Application No. PCT/JP2018/036363 dated Mar. 5, 2020. (3 pages).

Tanida et al., "Attempt to identify panic in terms of heart rate acceleration response during braking", ResearchGate, Aug. 15, 2001, vol. 37, No. 4 (01), pp. 159-168. Cited in IPRP2. with English Abstract. (11 pages).

Notification of Transmittal of Translation of the International Preliminary Report on Patentability (Form PCT/IB/338) issued in counterpart International Application No. PCT/JP2018/036363 dated Apr. 1, 2021 with Form PCT/IPEA/409. (5 pages).

\* cited by examiner

SYSTEM FOR ESTIMATING POTENTIAL RISK AREA WHEN VEHICLE IS TRAVELING

CROSS-REFERENCE TO RELATED APPLICATION(S)

This application is a continuation of International Patent Application No. PCT/JP2018/036363 filed on Sep. 28, 2018, the entire disclosures of which are incorporated herein by reference.

BACKGROUND OF THE INVENTION

Field of the Invention

The present invention relates to an information providing system, a server, a method, and a non-transitory computer-readable storage medium storing a program for providing information regarding vehicle traveling.

Description of the Related Art

In recent years, a system is known in which the state of a driver is estimated based on bio-information of an occupant while driving a vehicle, and a warning is given as necessary. In PTL 1, a technique is described in which the physical state of a driver is estimated using a heart rate as the bio-information and a road load amount. Also, it is also known that the bio-information of an occupant is used not only to estimate the state of a driver, but is used for estimating a risk caused due to movement of a vehicle (PTL 2).

CITATION LIST

Patent Literature

PTL 1: Japanese Patent No. 4514372
PTL 2: Japanese Patent No. 6301758

SUMMARY OF THE INVENTION

Technical Problem

PTL 2 describes a technique in which if it is determined that a risk event has occurred using vehicle body information (such as a steering operation, a braking operation, or acceleration), a threshold value that is likely to result in a risky behavior is set for a value of bio-information at a point in time before the risk event occurrence time. However, there may be cases where the occupant intentionally performs sudden acceleration and sudden deceleration while performing driving. It is highly possible that the processing load will be excessively increased if the vehicle body information is used to determine risk events even in such cases.

The present invention aims to provide an information providing system, a server, a method, and a non-transitory computer-readable storage medium storing a program for reducing the processing load when estimating a potential risk area when a vehicle is traveling.

Solution to Problem

An information providing system according to the present invention is an information providing system including a vehicle and a server, the information providing system comprising: an accepting unit configured to accept a reference heart rate level as a condition for displaying a risk map; an acquiring unit configured to acquire heart rate data of an occupant of the vehicle acquired by a wearable terminal attached to the occupant; a storing unit configured to store the heart rate data acquired by the acquiring unit; a specifying unit configured to specify a traveling state of the vehicle corresponding to a changing portion in which the amount of change in heart rate indicated by the heart rate data that satisfies the reference level accepted by the accepting unit, out of the heart rate data stored in the storing unit, is larger than a threshold value; an estimating unit configured to estimate the position of the vehicle at a point in time traced back by a predetermined time from the time corresponding to the changing portion as a risk area in which an event that causes the change in heart rate has occurred, based on the traveling state of the vehicle specified by the specifying unit, and a generating unit configured to generate the risk map in which the risk region estimated by the estimating unit is identifiably displayed, wherein the server includes the acquiring unit, the storing unit, the specifying unit, the estimating unit, and the generating unit.

Also, a method according to the present invention is a method to be executed in an information providing system including a vehicle and a server, the method comprising: an accepting step of accepting a reference heart rate level as a condition for displaying a risk map, an acquiring step of the server acquiring heart rate data of an occupant of the vehicle acquired by a wearable terminal attached to the occupant, and a storing step of the server storing the heart rate data acquired in the acquiring step, a specifying step of the server specifying a traveling state of the vehicle corresponding to a changing portion in which the amount of change in heart rate indicated by the heart rate data that satisfies the reference level accepted in the accepting step, out of the heart rate data stored in the storing step, is larger than a threshold value, an estimating step of the server estimating the position of the vehicle at a point in time traced back by a predetermined time from the time corresponding to the changing portion as a risk area in which an event that causes the change in heart rate has occurred, based on the traveling state of the vehicle specified in the specifying step, and a generating step of the server generating the risk map in which the risk region estimated in the estimating step is identifiably displayed.

Also, a server according to the present invention is a server comprising: an acquiring unit configured to acquire heart rate data of an occupant of a vehicle; a storing unit configured to store the heart rate data acquired by the acquiring unit; a specifying unit configured to specify a traveling state of the vehicle corresponding to a changing portion in which the amount of change in heart rate is larger than a threshold value, the heart rate being indicated by heart rate data that satisfies a reference level accepted by accepting unit for accepting the reference level of the heart rate, as a condition for displaying a risk map, out of the heart rate data stored in the storing unit; an estimating unit configured to estimate the position of the vehicle at a point in time traced back by a predetermined time from the time corresponding to the changing portion as a risk area in which an event that causes the change in heart rate has occurred, based on the traveling state of the vehicle specified by the specifying unit; and a generating unit configured to generate the risk map in which the risk area estimated by the estimating unit is identifiably displayed.

Also, a method according to the present invention is a method to be executed in a server, the method comprising: an acquiring step of acquiring heart rate data of an occupant of a vehicle; a storing step of storing the heart rate data acquired in the acquiring step; a specifying step of specifying a traveling state of the vehicle corresponding to a changing portion in which the amount of change in heart rate is larger than a threshold value, the heart rate being indicated by heart rate data that satisfies a reference level accepted by the accepting unit configured to accept the reference level of the heart rate, as a condition for displaying a risk map, out of the heart rate data stored in the storing step; an estimating step of estimating the position of the vehicle at a point in time traced back by a predetermined time from the time corresponding to the changing portion as a risk area in which an event that causes the change in heart rate has occurred, based on the traveling state of the vehicle specified in the specifying step; and a generating step of generating the risk map in which the risk area estimated in the estimating step is identifiably displayed.

Also, a storage medium according to the present invention is a non-transitory computer-readable storage medium storing a program causing a computer to function as: an acquiring unit configured to acquire heart rate data of an occupant of a vehicle; a storing unit configured to store the heart rate data acquired by the acquiring unit; a specifying unit configured to specify a traveling state of the vehicle corresponding to a changing portion in which the amount of change in heart rate is larger than a threshold value, the heart rate being indicated by heart rate data that satisfies a reference level accepted by accepting unit configured to accept the reference level of the heart rate, as a condition for displaying a risk map, out of the heart rate data stored in the storing unit; an estimating unit configured to estimate the position of the vehicle at a point in time traced back by a predetermined time from the time corresponding to the changing portion as a risk area in which an event that causes the change in heart rate has occurred, based on the traveling state of the vehicle specified by the specifying unit; and a generating unit configured to generate the risk map in which the risk area estimated by the estimating unit is identifiably displayed.

Advantageous Effects of Invention

According to the present invention, the processing load when estimating a potential risk area when a vehicle is traveling can be reduced. Other features and advantages of the present invention will be apparent from the following description taken in conjunction with the accompanying drawings. Note that the same reference numerals denote the same or like components throughout the accompanying drawings.

BRIEF DESCRIPTION OF THE DRAWINGS

The accompanying drawings, which are incorporated in and constitute a part of the specification, illustrate embodiments of the invention and, together with the description, serve to explain principles of the invention.

DESCRIPTION OF THE EMBODIMENTS

Figure 1:
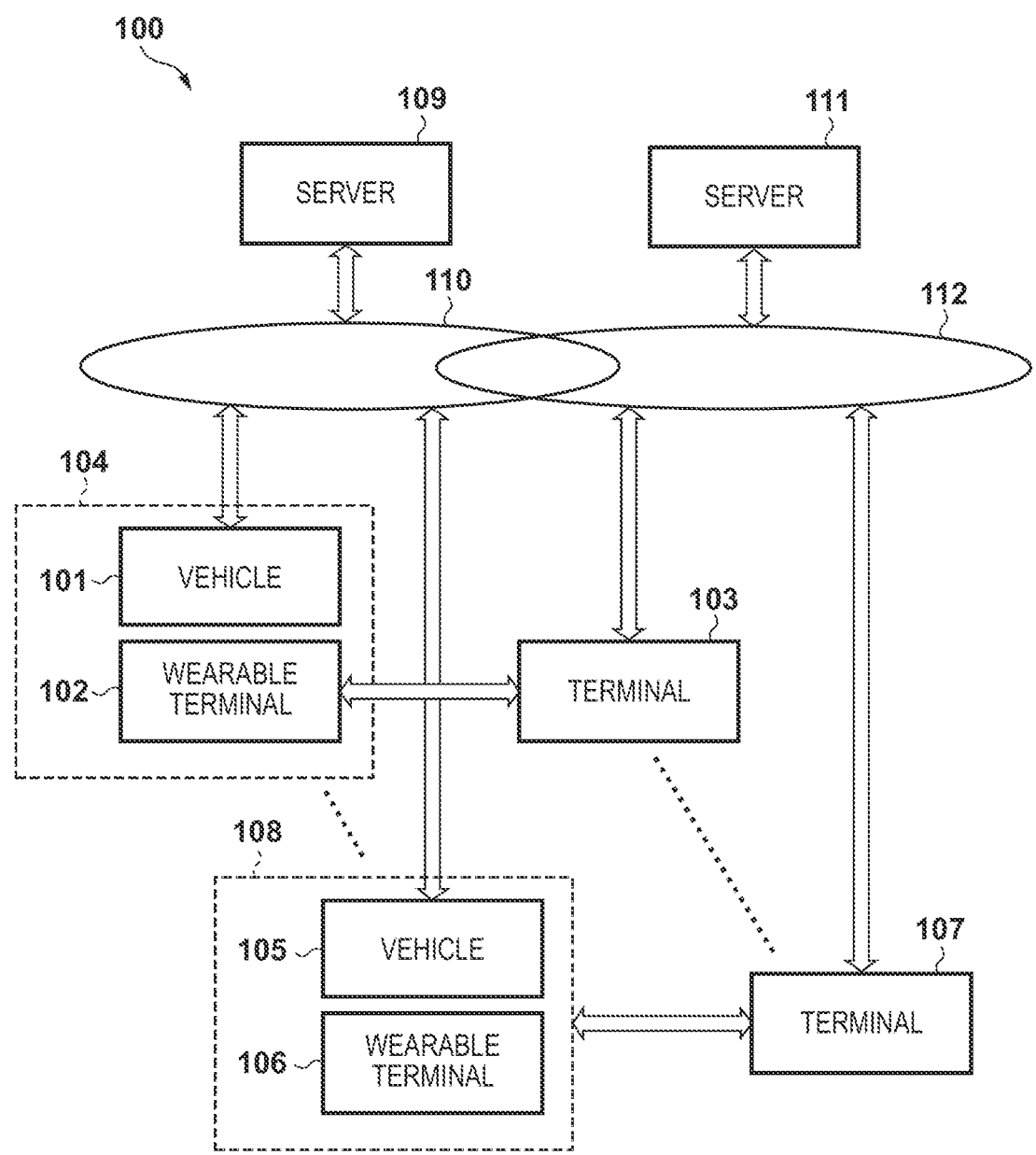
FIG. 1 is a diagram illustrating a configuration of an information providing system.

Preferred embodiments of the present invention will now be described hereinafter, with reference to the accompanying drawings. Note that the same constituent elements are given the same reference numerals, and a description thereof is omitted.

FIG. 1 is a diagram illustrating a configuration of an information providing system in the present embodiment. An information providing system 100 includes a network 110 for collecting vehicle information such as speed and position information from a vehicle 101, and a network 112 for performing data communication between a server and a terminal. The vehicle 101 is a motorcycle, which is a straddle type vehicle, or an automatic four-wheel vehicle, for example, and in the present embodiment, a description will be given assuming that the vehicle 101 is a motorcycle, as an example. The network 110 is a vehicle communication network in which vehicles 101 and 105 and a server 109 are connected so as to be able to communicate to each other, and pieces of vehicle information of the vehicles 101 and 105 are transmitted to the server 109. Also, the network 110 can also be connected to networks of other systems such as a traffic system and a weather system. The server 109 can provide various types of services, such as traffic information, weather information, regarding traveling of the vehicle, to a user of the information providing system 100, and provides a potential risk map generation service, for example.

The network 112 is a data communication network in which terminals 103 and 107 and a server 111 are connected so as to be able to communicate to each other, and data communication is performed between the terminals 103 and 107 and the server 111. The network 112 may be the Internet, for example. Also, the network 110 and the network 112 are connected to each other, and mutual communication can be performed between the server 109 and the server 111, and between the terminals 103 and 107 and the server 109. For example, the terminals 103 and 107 can receive services provided by the respective servers. Wearable terminals 102 and 106 are terminals that are to be attached to a human body and are for measuring bio-information such as a heart rate, a pulse, and a blood pressure. In the present embodiment, the wearable terminals 102 and 106 measure and acquire the heart rates of occupants of the vehicles 101 and 105 as the bio-information. The server 111 is a server for providing a service in which bio-information measured by the wearable terminals 102 and 106 is utilized.

In the information providing system 100, an occupant A of the vehicle 101 wears the wearable terminal 102, and drives the vehicle 101 while the heart rate being measured. The vehicle information of the vehicle 101 at the time of driving is transmitted to the server 109. After ending driving, the occupant A of the vehicle 101 directly connects the wearable terminal 102 to a terminal 103 such as a PC by a USB or a cable, activates an application corresponding to the wearable terminal 102, and outputs heart rate data (log data) obtained as a result of the measurement to the terminal 103. Then, the occupant A uploads the heart rate data from the terminal 103 to the server 111. Also, an occupant B of the vehicle 105 wears the wearable terminal 106, and drives the vehicle 105 while the heart rate being measured. The vehicle information of the vehicle 105 at the time of driving is transmitted to the server 109. After ending driving, the occupant B of the vehicle 105 directly connects the wearable terminal 106 to a terminal 107 such as a PC by a USB or a cable, activates an application corresponding to the wearable terminal 106, and outputs heart rate data (log data) obtained as a result of the measurement to the terminal 107. Then, the occupant B uploads the heart rate data from the terminal 107 to the server 111.

In FIG. 1, the vehicle 101, the wearable terminal 102, and the terminal 103 are associated with the occupant A (e.g., owned by the occupant A), and the vehicle 101 and the wearable terminal 102 integrally move while the vehicle 101 being driven, as shown by a broken line 104. The terminal 103 is an information processing apparatus such as a PC installed at a home of the occupant A or a mobile terminal owned by the occupant A, for example. Also, the vehicle 105, the wearable terminal 106, and the terminal 107 are associated with the occupant B (e.g., owned by the occupant B), and the vehicle 105 and the wearable terminal 106 integrally move while the vehicle 105 being driven, as shown by a broken line 108. The terminal 107 is an information processing apparatus such as a PC installed at a home of the occupant B or a mobile terminal owned by the occupant B, for example. Although, in FIG. 1, a configuration of two sets of apparatuses regarding the occupant A and the occupant B is shown, the description of each set of apparatuses is the same regarding the configuration of any one set, or the configuration of three or more sets. In the following description, a description will be given regarding a set of the occupant A, the vehicle 101, the wearable terminal 102, and the terminal 103, out of the two sets, as a representative example, unless otherwise specified. Also, in FIG. 1, the server 109 and the server 111 are illustrated as separate servers, but may be integrally configured, or each server may also be configured by a plurality of apparatuses.

In the present embodiment, heart rate data is collected from each occupant while the vehicle is traveling, and a potential risk map is generated that indicates locations at which potentially serious incidents have occurred, based on the collected pieces of heart rate data. That is, in the present embodiment, attention is given to the relevance between an event of a potentially serious incident and the heart rate of an occupant, and a potential risk map is generated using the heart rate data acquired while the vehicle is traveling.

Figure 2:
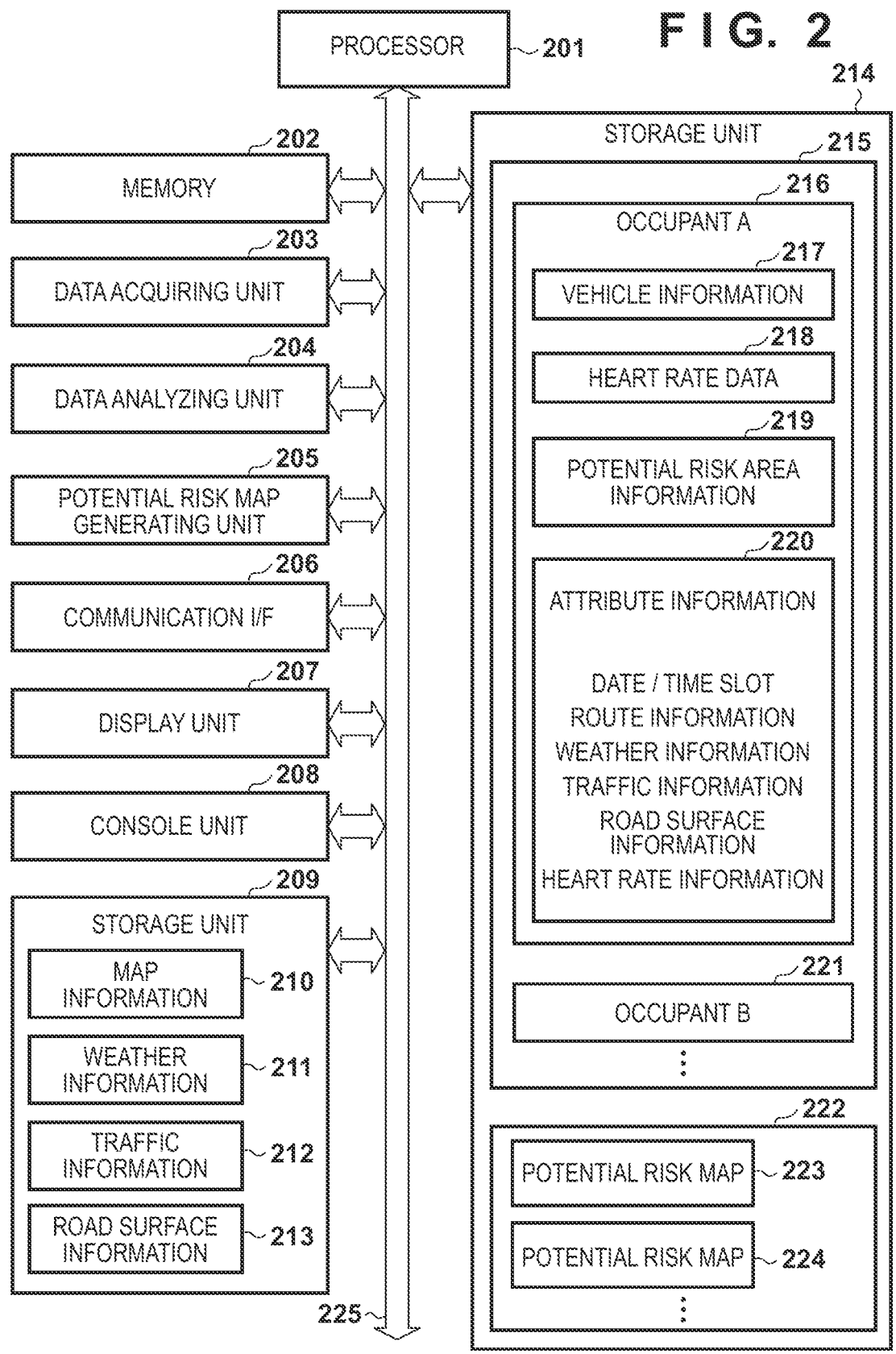
FIG. 2 is a diagram illustrating a block configuration of a server.

FIG. 2 is a diagram illustrating a block configuration of the server 109. A processor 201 performs overall control on the server 109. For example, the processor 201 controls the blocks via a bus 225 by loading a control program stored in a storage unit 209 to a memory 202 and executing the program, and with this, realizes the operations in the present embodiment. A data acquiring unit 203 acquires vehicle information transmitted from the vehicle 101 via a communication interface (I/F) 206, and stores the vehicle information in a storage unit 214. There may be cases where the data acquiring unit 203 performs extraction (thinning) regarding the acquired vehicle information at predetermined time intervals in order to perform alignment with other data on the time axis, and stores the extracted vehicle information in the storage unit 214. Also, the data acquiring unit 203 acquires data form another server. For example, the data acquiring unit 203 acquires heart rate data from the server 111. Also, the data acquiring unit 203 can also acquire pieces of information such as map information, weather information, traffic information, and road surface information from a server of another traffic system. A data analyzing unit 204 estimates a potential risk area by analyzing the heart rate data acquired by the data acquiring unit 203, and a potential risk map generating unit 205 generates a potential risk map based on an estimated potential risk area. The analysis of heart rate data, and the generation of a potential risk map will be described later. The units from the data acquiring unit 203 to the potential risk map generating unit 205 may each include a processor such as a CPU or GPU. Also, in FIG. 2, the units from the data acquiring unit 203 to the potential risk map generating unit 205 are illustrated as separate blocks, but may be integrally configured.

The communication I/F 206 is configured according to the communication medium of the network such as wireless or wired network. A display unit 207 is a display, for example, and displays various types of user interface screens. A console unit 208 is a keyboard or a pointing device, for example, and accepts operations from a user regarding settings and instructions. A storage unit 209 stores various programs and parameters for operating the server 109 and information to be used in the present embodiment. The storage unit 209 stores map information 210, weather information 211, traffic information 212, and road surface information 213, for example. The map information 210 is map information acquired by the data acquiring unit 203 from a map database of another server, for example, and includes a place-name, a name, road width information, and the like. Also, the weather information 211 is weather information for each district that is acquired by the data acquiring unit 203 from a weather database of another server, for example, and includes information such as temperature, humidity, orientation of the sun, and visibility due to haze, in addition to weather information such as rain and fine weather. The traffic information 212 is traffic jam information acquired by the data acquiring unit 203 from a traffic jam information database of another server, for example, and includes construction information, event information, traffic regulation information, and the like, in addition to the traffic jam information. The road surface information 213 is road surface freeze distribution information acquired by the data acquiring unit 203 from another server, for example, and includes information regarding the road being paved or not, paint, floating sand, and the like, in addition to the road surface freeze distribution information.

A personal database 215 for each occupant and a potential risk map database 222 generated by the potential risk map generating unit 205 are constructed in the storage unit 214. In FIG. 2, a personal database 216 associated with the occupant A and a database personal 221 associated with the occupant B are illustrated as the personal database 215. The personal database 221 associated with the occupant B is configured similarly to the personal database 216 associated with the occupant A. In the following, the personal database 216 associated with the occupant A will be described as a representative example of the database associated with each occupant, unless otherwise specified.

Figure 11:
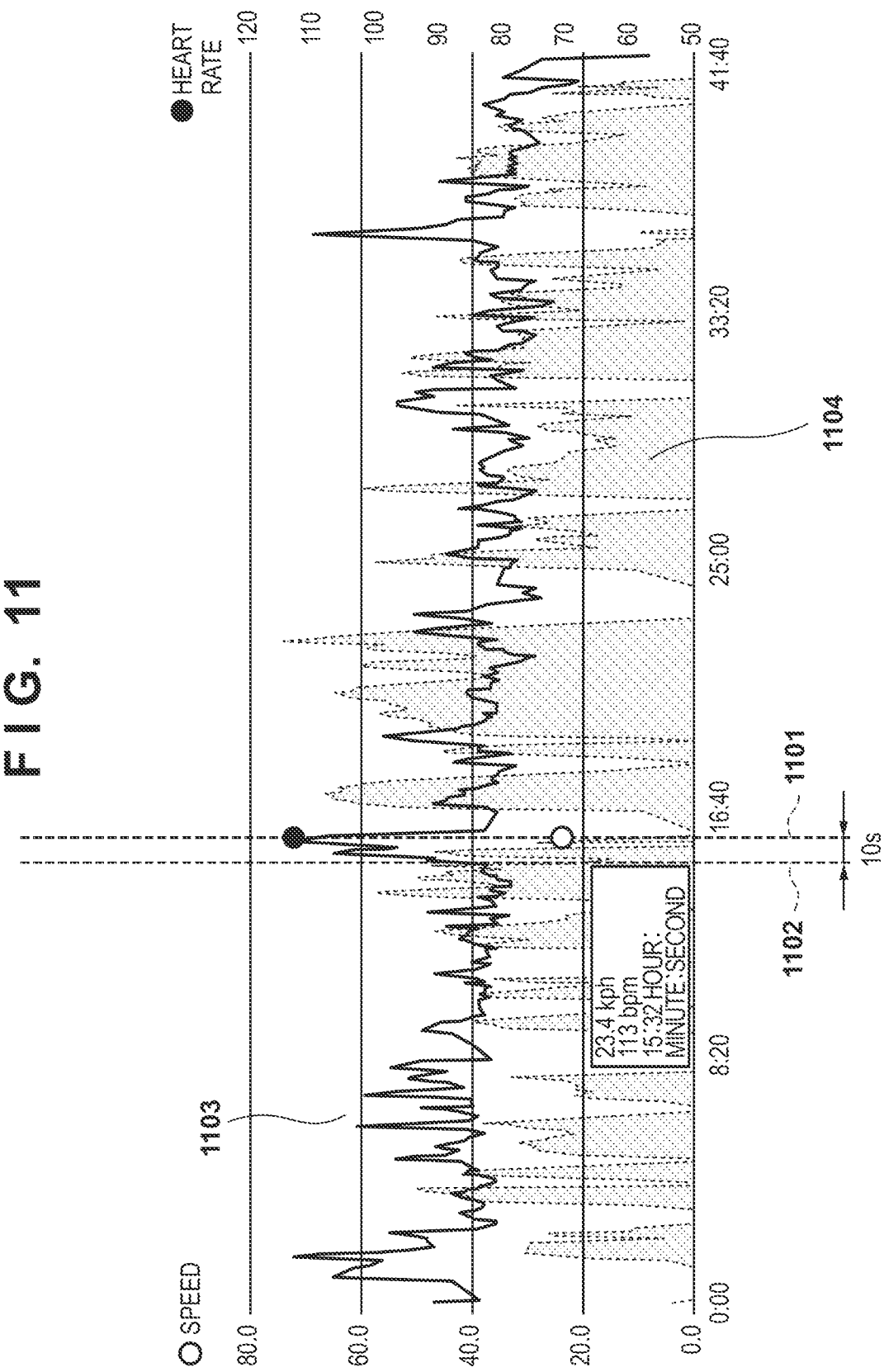
FIG. 11 is a diagram illustrating heart rate data.

The personal database 216 includes vehicle information 217, heart rate data 218, potential risk area information 219, and attribute information 220. The vehicle information 217 is vehicle information acquired by the data acquiring unit 203, and includes speed, GPS information, acceleration, and various types of sensor information, for example. The heart rate data 218 is data as shown in FIG. 11, for example. The data is shown as continuous heart rate data along a time axis in FIG. 11, but the data is stored as discrete data taken at predetermined time intervals. The heart rate data 218 is log data measured by the wearable terminal 102 in a period from when the occupant A started driving of the vehicle 101 until the end of driving. The potential risk area information 219 is information regarding an area in which a risk is estimated to be potentially present, which is obtained from the result of analysis performed by the data analyzing unit 204 on the heart rate data 218. The potential risk area information 219 is represented by the map information 210 or position information obtained by the GPS, for example. The attribute information 220 is attribute information acquired regarding traveling of the vehicle 101 performed by the occupant A, and includes a date/time slot, route information, weather information, traffic information, road surface information, and heart rate information, for example. The date/time slot, route information, weather information, traffic information, and road surface information are acquired from the data acquiring unit 203, map information 210, weather information 211, traffic information 212, and road surface information 213. Also, the heart rate information is information acquired from the heart rate data 218, and includes a maximum value, a minimum value, an average value, and a maximum change amount of the heart rate, for example. Also, each information included in the attribute information 220 is stored such that the source from which the information has been acquired, such as the map information 210, weather information 211, traffic information 212, or road surface information 213, for example, can be identified.

In FIG. 2, the personal database 216 associated with the occupant A and the personal database 221 associated with the occupant B are illustrated, but there are cases where a plurality of personal databases are constructed in association with the occupant A. For example, a personal database is constructed based on vehicle information and heart rate data that have been acquired when the occupant A performed driving from A City to B City on February 1, and on the other hand, a personal database is constructed based on vehicle information and heart rate data that have been acquired when the occupant A performed driving from X City to Y City on February 3. That is, there are cases where a plurality of databases corresponding to respective past driving histories of one occupant are constructed in the personal database 215, in addition to the personal databases associated with a plurality of occupants.

The potential risk map database 222 is a potential risk map generated by the potential risk map generating unit 205. The potential risk map generating unit 205 can generate various types of potential risk maps 223 and 224 based on predetermined information included in the attribute information 220. For example, the potential risk map generating unit 205 generates a potential risk map by extracting the potential risk area information 219, in a personal database, corresponding to a specific route and a time slot of 6:00 to 8:00 early in the morning. Also, the potential risk map generating unit 205 generates a potential risk map by extracting the potential risk area information 219 in personal databases associated with occupants whose average values of the heart rate are almost at the same level in a predetermined range, for example.

The estimation of a potential risk area in the present embodiment will be described. Here, it is assumed that the heart rate data as shown in FIG. 11 is acquired by the data acquiring unit 203. According to FIG. 11, the heart rate has increased to 113 bpm (beats per minute) at time 15:32. It is known that, in general, the heart rate of an occupant who is driving a vehicle increases not at the same time as the event occurrence time such as sudden rushing out from an unexpected direction, for example, but at a time at which a predetermined time has elapsed from the occurrence time. By paying attention to such a point, in the present embodiment, a point in time traced back by a predetermined time from the time at which the heart rate has increased is determined as an event occurrence time. Also, the location at the event occurrence time is specified from the vehicle traveling state (such as position and speed) at a point in time at which the heart rate has increased, and this location is estimated as a potential risk area. For example, in FIG. 11, a point in time 1102 traced back by a predetermined time, 10 seconds for example, from a point in time 1101 at which the heart rate has increased is determined as the event occurrence time.

There are cases where acceleration and deceleration information of a vehicle is used to estimate a potentially serious incident, in general, but even in cases where sudden deceleration or sudden acceleration is performed, this operation may be performed by own intention of the occupant. Therefore, the acceleration and deceleration information of a vehicle is not necessarily directly associated with a potentially serious incident. As shown in FIG. 11, although there are many points at which the speed has steeply changed, these points are not necessarily linked to the increase in heart rate. That is, it is necessary to perform narrowing-down of data from the acceleration and deceleration information in a period from the start to the end of traveling of the vehicle to portions corresponding to potentially serious incidents, and the processing load is large. On the other hand, according to the present embodiment, the potential risk area is estimated using a pint in time at which the heart rate has increases as a reference, the narrowing-down of data as described above is not needed, and therefore the processing load can be largely reduced.

Figure 3:
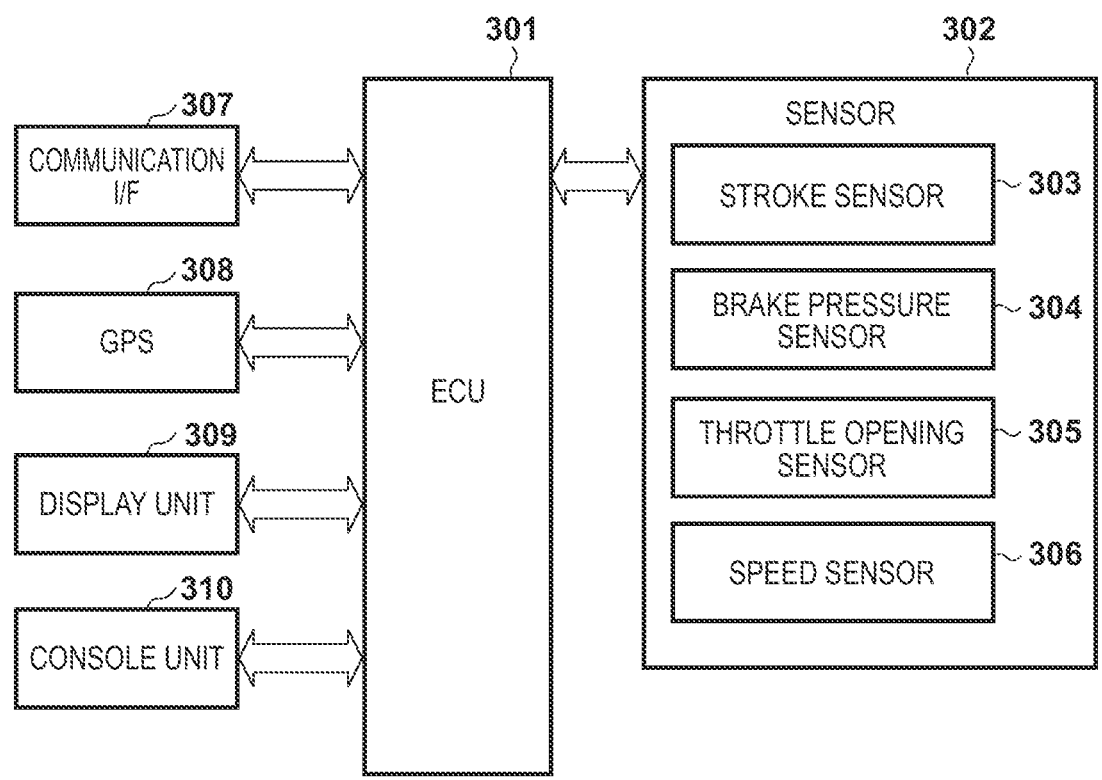
FIG. 3 is a diagram illustrating a block configuration of a vehicle.

FIG. 3 is a diagram illustrating a block configuration of the vehicle 101. FIG. 3 only illustrates main block constituent elements according to the present embodiment, but may include, not limited to the illustrated blocks, constituent elements of a general motorcycle. Also, FIG. 3 shows a configuration in which the vehicle 101 is a motorcycle that is a straddle type vehicle, but may also be a configuration in which the vehicle 101 is an automatic four-wheel vehicle.

The vehicle 101 includes various types of sensors 302 for detecting the behavior of the vehicle 101, a GPS 308 for acquiring the position information of the vehicle 101, a display unit 309 including a panel for displaying information regarding the behavior of the vehicle 101, various user interface screens, and the like, a console unit 310 for accepting operations made by an occupant, and an ECU 301. The sensors 302 includes stroke sensors 303 for detecting stroke amounts of suspensions of a front wheel and a rear wheel, brake pressure sensors for detecting pressures of liquid to brakes of the front wheel and the rear wheel, a throttle opening sensor 305 for detecting an accelerator operation amount, and a speed sensor 306. The ECU 301 converts the detection information from the sensors 302 and the GPS 308 to data for transmission, and transmits the converted data to the server 109 via a communication I/F 307 as the vehicle information.

Figure 4:
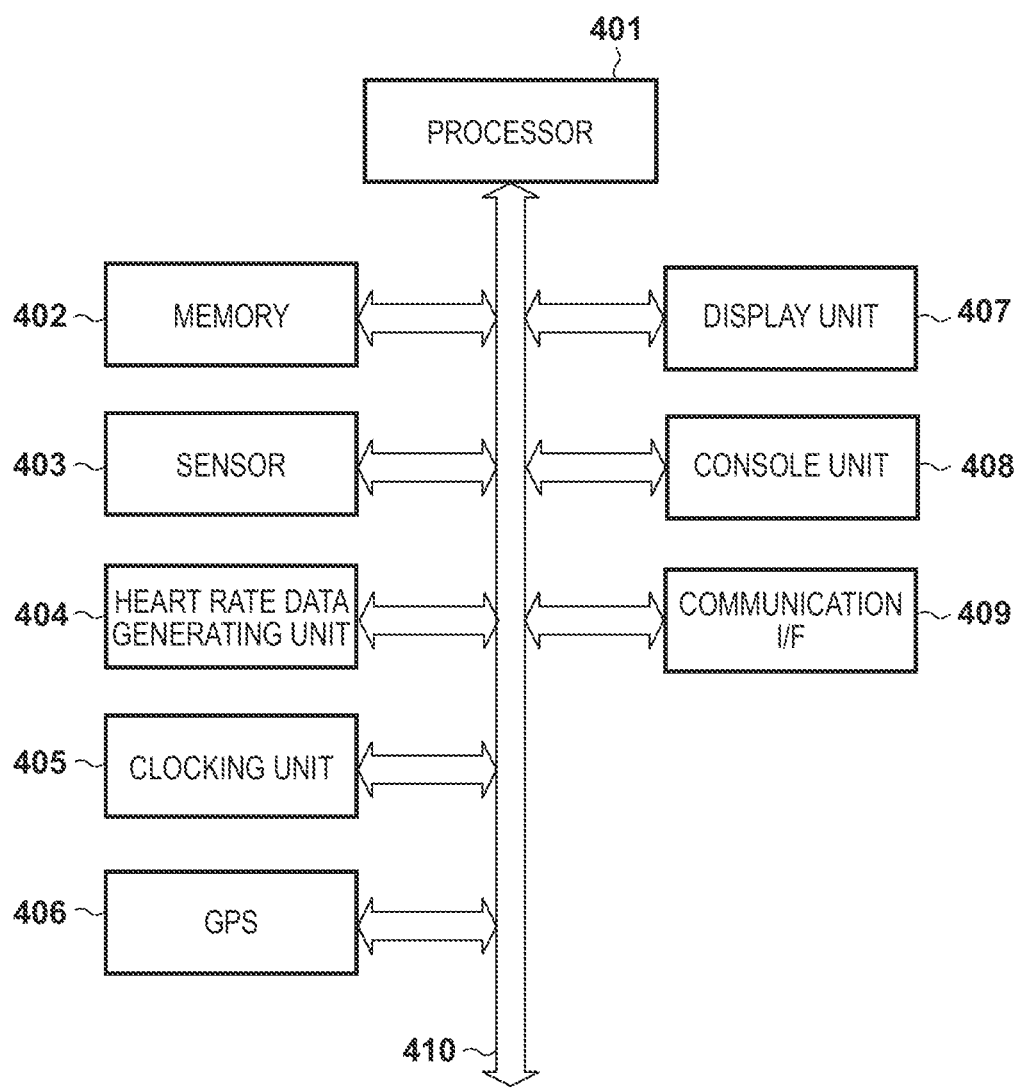
FIG. 4 is a diagram illustrating a configuration of a wearable terminal.

FIG. 4 is a diagram illustrating a configuration of the wearable terminal 102. In the present embodiment, the wearable terminal 102 is a wrist watch-type apparatus to be attached to the occupant A when the vehicle 101 is traveling, for example, and measures the heart rate of the occupant A. A processor 401 performs overall control on the wearable terminal 102, controls the blocks via a bus 410, for example, and realizes the operations in the present embodiment. A memory 402 stores programs (such as an application program and a driver) and parameters for the wearable terminal 102 to operate, and generated heart rate data. A sensor 403 is a sensor for monitoring the heart rate, and is an optical sensor that reads a blood flow amount using an LED, for example.

A heart rate data generating unit 404 generates heart rate data by shaping a heart rate signal monitored by the sensor 403. A clocking unit 405 acquires the current time, and has a clocking function. A GPS 406 acquires position information of the wearable terminal 102. A display unit 407 is a display unit such as a liquid crystal display, and displays a user interface screen for executing and setting various types of functions of the wearable terminal 102. The console unit 408 accepts a user operation performed using a power switch and a setting switch, or by a touch operation made on the display unit 407. A communication I/F 409 is a communication interface with external apparatuses according to the communication medium of the network such as wireless or wired network, and direct connection to the terminal 103 using a USB cable or short-range wireless communication therewith are possible, for example.

Figure 5:
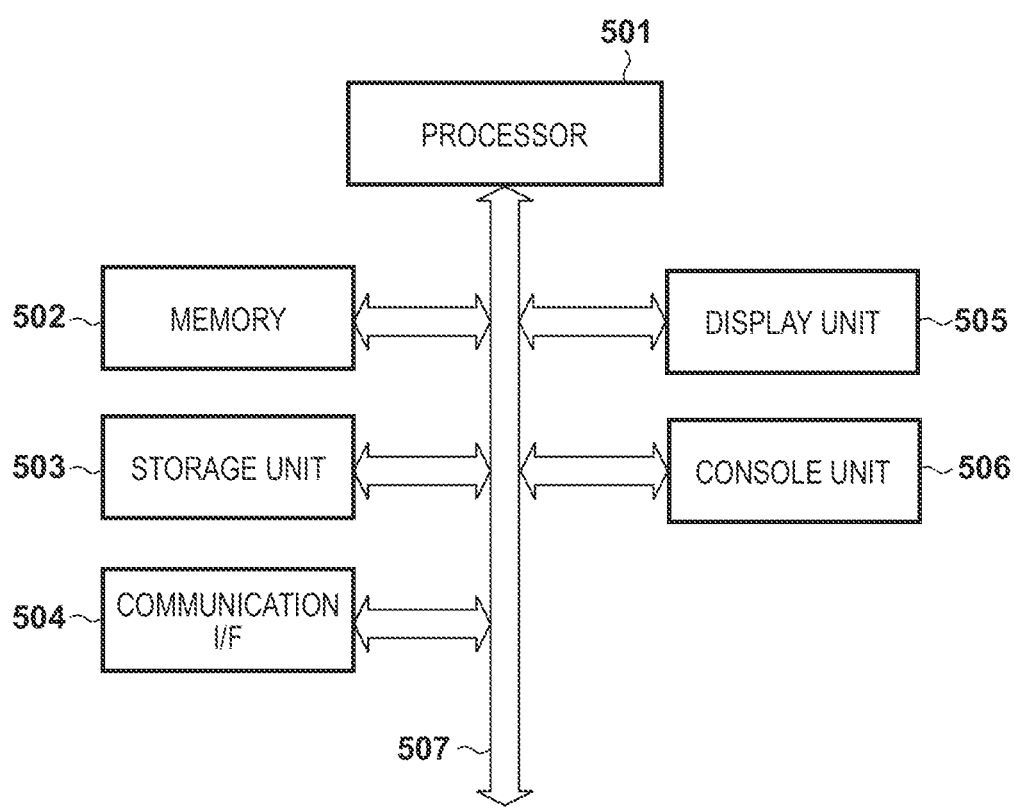
FIG. 5 is a diagram illustrating a configuration of a terminal and the server.

FIG. 5 is a diagram illustrating a configuration of the terminal 103 and the server 111. The terminal 103 and server 111 have a configuration as a standard information processing apparatus such as a PC. A processor 501 performs overall control on the terminal 103 or the server 111, controls the blocks via a bus 507 by loading a program stored in a storage unit 503 to a memory 502 and executing the program, and realizes the operations in the present embodiment, for example. The storage unit 503 stores programs for operating the terminal 103. For example, in the case of the terminal 103, the storage unit 503 stores an application for acquiring heart rate data from the wearable terminal 102 and uploading the heart rate data to the server 111. Also, in the case of server 111, for example, the storage unit 503 stores a service application, for providing a service corresponding to the wearable terminal 102, that can be downloaded to the terminal 103.

A communication I/F 504 is a communication interface with external apparatuses according to the communication medium of the network such as wireless or wired network, and includes communication interfaces respectively corresponding to the USB, the LAN cable, the Wifi (registered trademark), and the like. The display unit 505 includes a display and the like, and displays various interface screens. A console unit 506 includes a keyboard, a pointing device, and the like, and accepts user operations regarding settings and instructions. The terminal 103 and server 111 may include constituent elements other than those shown in FIG. 5, and when the terminal 103 is a mobile wireless terminal, the terminal 103 further includes a microphone, a speaker, and the like, for example.

Figure 6:
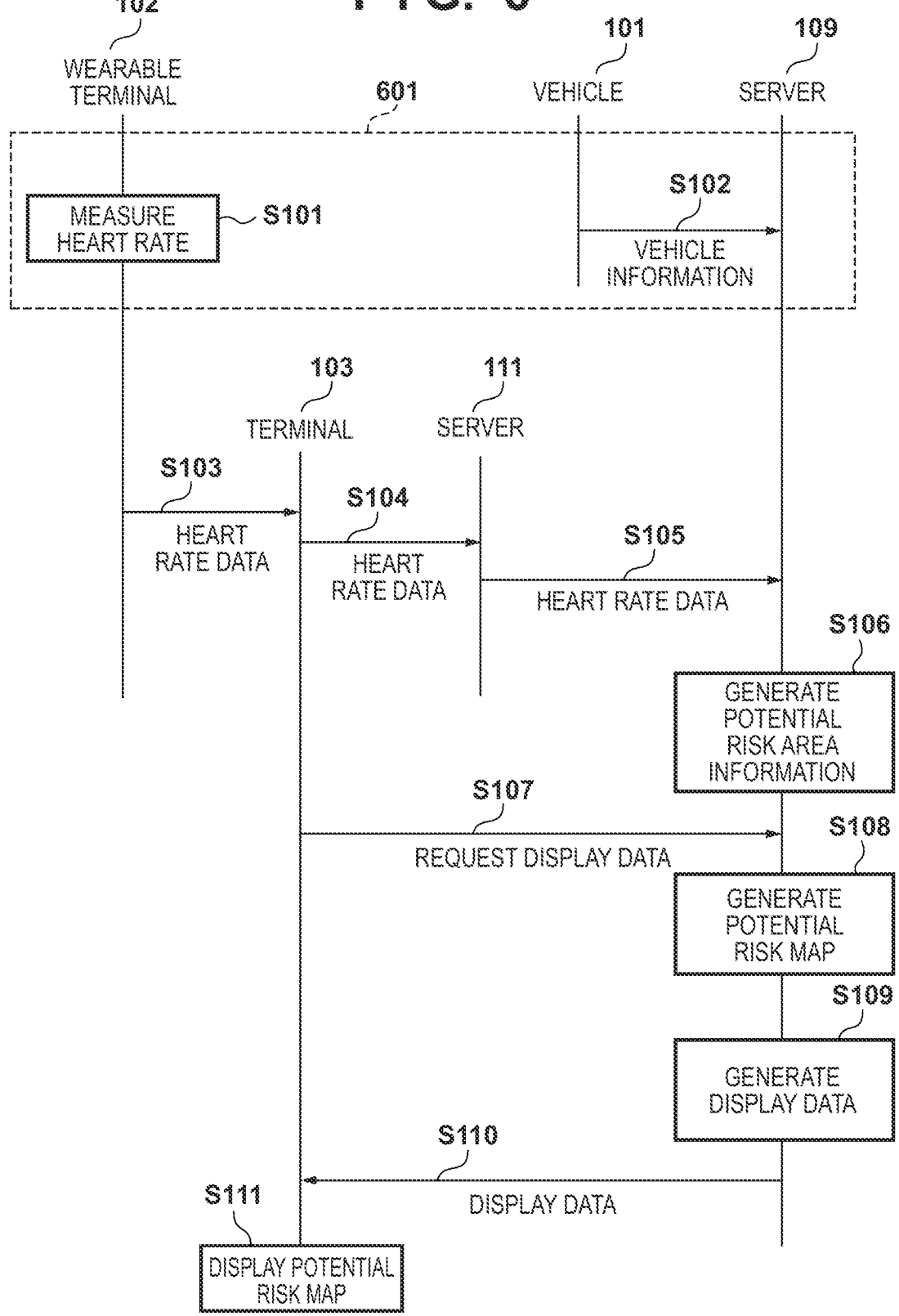
FIG. 6 is a diagram illustrating a processing flow in the information providing system.

FIG. 6 is a diagram illustrating a processing flow until a potential risk map being displayed in the information providing system 100. The occupant A wears the wearable terminal 102 when driving the vehicle 101 along a commuting route or the like. Also, when starting driving, the occupant A inputs an ID and the like in order to start using the information providing system 100 via the console unit 310 of the vehicle 101. Such an ID is commonly recognized in the service provided by the server 109 and the service provided by the server 111, and with this ID, the server 109 can associate the vehicle information transmitted from the vehicle 101 with the heart rate data acquired from the server 111. The input ID is transmitted from the vehicle 101 to the server 109.

The occupant A starts log recording of the heart rate data performed by the wearable terminal 102 when started driving. As a result, in a driving period 601, the vehicle 101 transmits the vehicle information at any time, at predetermined time intervals, for example, to the server 109 (step S102), and the wearable terminal 102 monitors and measures the heart rate of the occupant A, and stores the heart rate data generated by the heart rate data generating unit 404 in the memory 402 (step S101). Time information regarding time measured by the clocking unit 405 and position information acquired by the GPS 406 are added to the heart rate data generated here.

The occupant A, upon ending the driving, ends the log recording of the heart rate data performed by the wearable terminal 102, connects the wearable terminal 102 to the terminal 103, and activates an application corresponding to the wearable terminal 102 on the terminal 103. Here, the occupant A inputs an ID that is the same as the ID that was input when starting driving of the vehicle 101, on the application. As a result of an operation made by the occupant A on the application, the heart rate data stored in the memory 402 of the wearable terminal 102 is downloaded to the terminal 103 (step S103). Also, as a result of an operation made by the occupant A on the application, the heart rate data is uploaded from the terminal 103 to the server 111 (step S104). The server 111 transmits the uploaded heart rate data and the ID to the server 109 (step S105). The server 109 stores the vehicle information transmitted from the vehicle 101 in step S102 and the heart rate data received from the server 111 in step S105 in the storage unit 214 while associating them based on the ID. The vehicle information 217 and heart rate data 218 in FIG. 2 correspond to the vehicle information and heart rate data here.

In the present embodiment, the heart rate data is once downloaded to the terminal 103, and thereafter uploaded from the terminal 103 to the server 111, but another configuration may be adopted. For example, a configuration may be adopted in which data can be moved between the wearable terminal 102 and the vehicle 101 using short-range wireless communication, a memory card, or the like. In such a configuration, when the wearable terminal 102 ends log recording of the heart rate, the heart rate data is moved from the wearable terminal 102 to the vehicle 101. Then, the heart rate data may be uploaded from the vehicle 101 to the server 111.

The server 109 generates potential risk area information by analyzing the heart rate data 218 stored in the storage unit 214, and stores the potential risk area information in the storage unit 214 (step S106). The potential risk area information generated here is position information such as an address such as "1-1, ABC", a place-name such as XYZ intersection, or the latitude and longitude. Alternatively, the potential risk area information may also be information indicating a certain range. The potential risk area information 219 in FIG. 2 corresponds to the potential risk area information generated here.

Thereafter, as a result of operations made by the occupant A, the terminal 103 requests display data for displaying the potential risk map to the server 109 (step S107). Hereinafter, the occupant that has ended driving of the vehicle 101 is also called as a user. The operations made by the user A include activating an application provided by the server 109 and selecting a menu item for displaying the potential risk map, for example. Also, the operations include a condition setting such as a time slot to be a target of the potential risk map, such as a time slot. The application activated when requesting the display data in step S107 may be different from the application that is activated when uploading the heart rate data to the server 111 in step S104, or may be executed by the same application.

When the terminal 103 has requested display data, the server 109 generates the potential risk map (step S108). The server 109 generates the potential risk map based on the potential risk area information 219 in the personal database stored in the storage unit 215, in accordance with the condition transmitted from the terminal 103. Also, the server 109 generates display data for allowing the terminal 103 to perform display based on the generated potential risk map (step S109), and transmits the display data to the terminal 103 (step S110). The terminal 103 displays the potential risk map in the display unit 505 based on the received display data (step S111).

Figure 7:
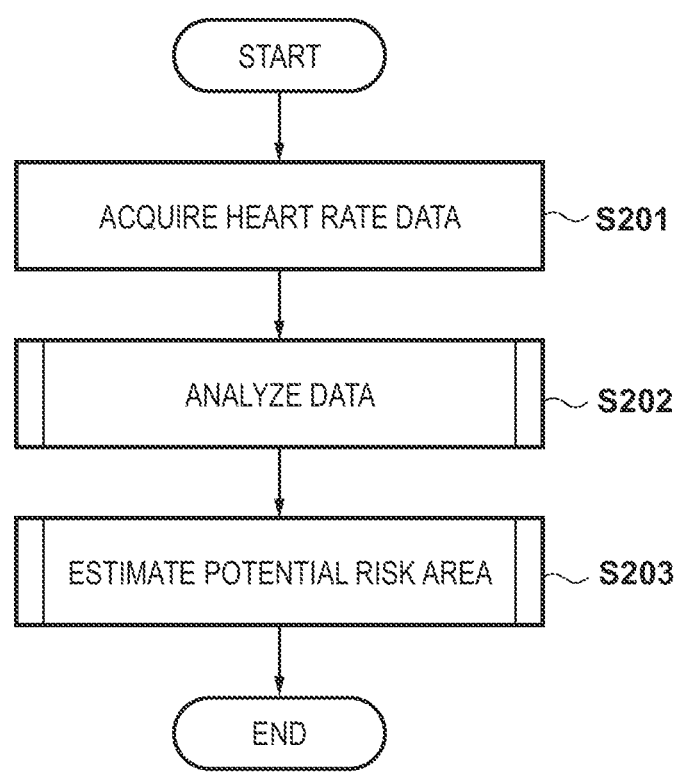
FIG. 7 is a flowchart illustrating processing for estimating a potential risk area.

FIG. 7 is a flowchart illustrating processing for estimating the potential risk area in the server 109. The processing in FIG. 7 corresponds to the processing in step S106 in FIG. 6. The processing in FIG. 7 is realized by the processor 201 executing a program that is loaded to the memory 202.

In step S201, the data acquiring unit 203 acquires heart rate data. The data acquiring unit 203 may acquire the heart rate data that has been transmitted from the server 111 and stored in the storage unit 214, or may acquire by requesting, with the ID corresponding to the occupant, the heart rate data to the server 111. The acquired heart rate data is data that is represented by two axes that are time information and a heart rate, as shown in FIG. 11, for example. In step S202, the data analyzing unit 204 analyzes the heart rate data acquired in step S201. Also, in step S203, the data analyzing unit 204 estimates the potential risk area based on the analysis result of the heart rate data. The processing in steps S202 and S203 will be described later. The processing in FIG. 7 is ended after step S203.

Figure 8:
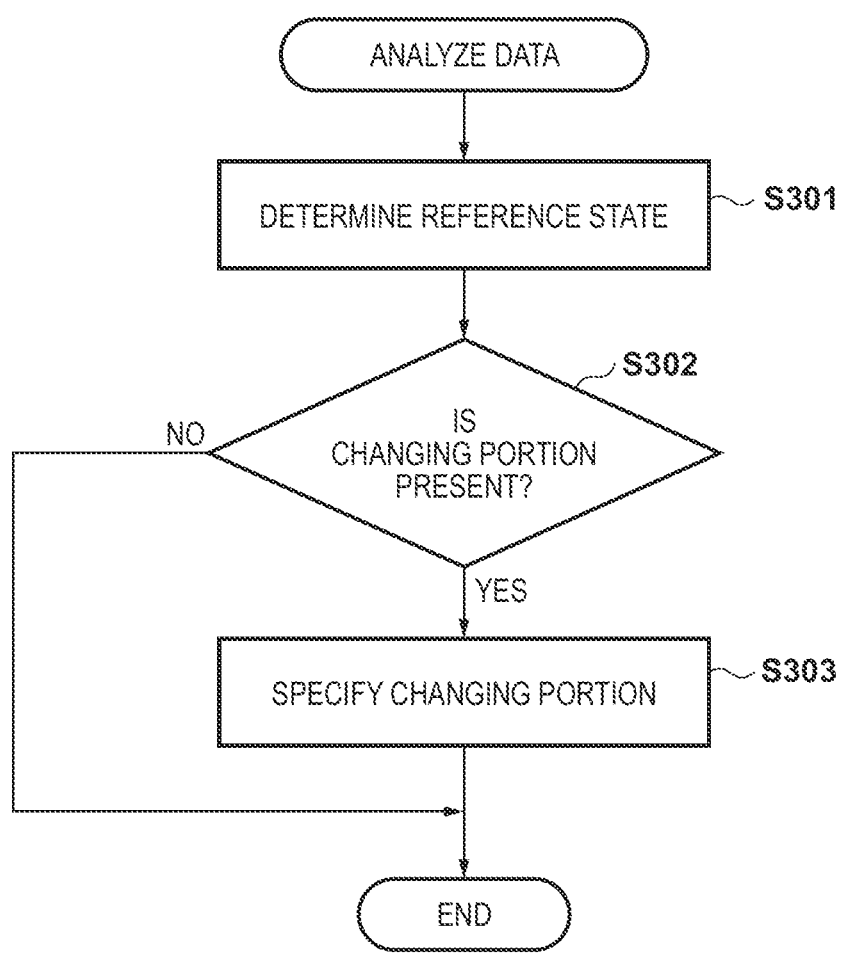
FIG. 8 is a flowchart illustrating processing of data analysis in step S102.

FIG. 8 is a flowchart illustrating processing of data analysis in step S202. In step S301, the data analyzing unit 204 determines the reference state of the occupant A based on the heart rate data acquired in step S201. Here, the reference state of the occupant A means a calm state of the occupant A, and in the present embodiment, is represented by an average value of the heart rate indicated by the heart rate data, for example. Also, it is possible to not use all of the heart rates of the heart rate data acquired in step S201 to calculate the average value. For example, only the heart rates in a range inside a predetermined variance centered about a value in the axis direction representing the heart rate may be used. Also, the median value or the like may be used instead of the average value. The data analyzing unit 204 stores the calculated value as the heart rate information representing the reference state of the occupant A in the attribute information 220 of the personal database 216.

In step S302, the data analyzing unit 204 determines whether or not a changing portion is present in which the heart rate changes in the transition of the heart rate indicated by the heart rate data acquired in step S201. The data analyzing unit 204 calculate the change amount (slope or the like) of the heart rate for each predetermined time unit from when the log recording has started, for example. If a portion in which the change amount is larger than a threshold value (steeply increasing portion) is present, it is determined that a changing portion is present. If it is determined that a changing portion is present in step S302, the processing is advanced to step S303, the data analyzing unit 204 specifies the changing portion using the corresponding time information, and ends the processing in FIG. 8. On the other hand, if it is determined that a changing portion is not present in step S302, it is determined that the occupant A keeps a calm state in the driving of the vehicle 101, and ends the processing in FIG. 8. Also, in this case, since the calm state having being kept in the driving, it is determined that a potential risk area was not present, and the processing in FIG. 7 is also ended.

Figure 9:
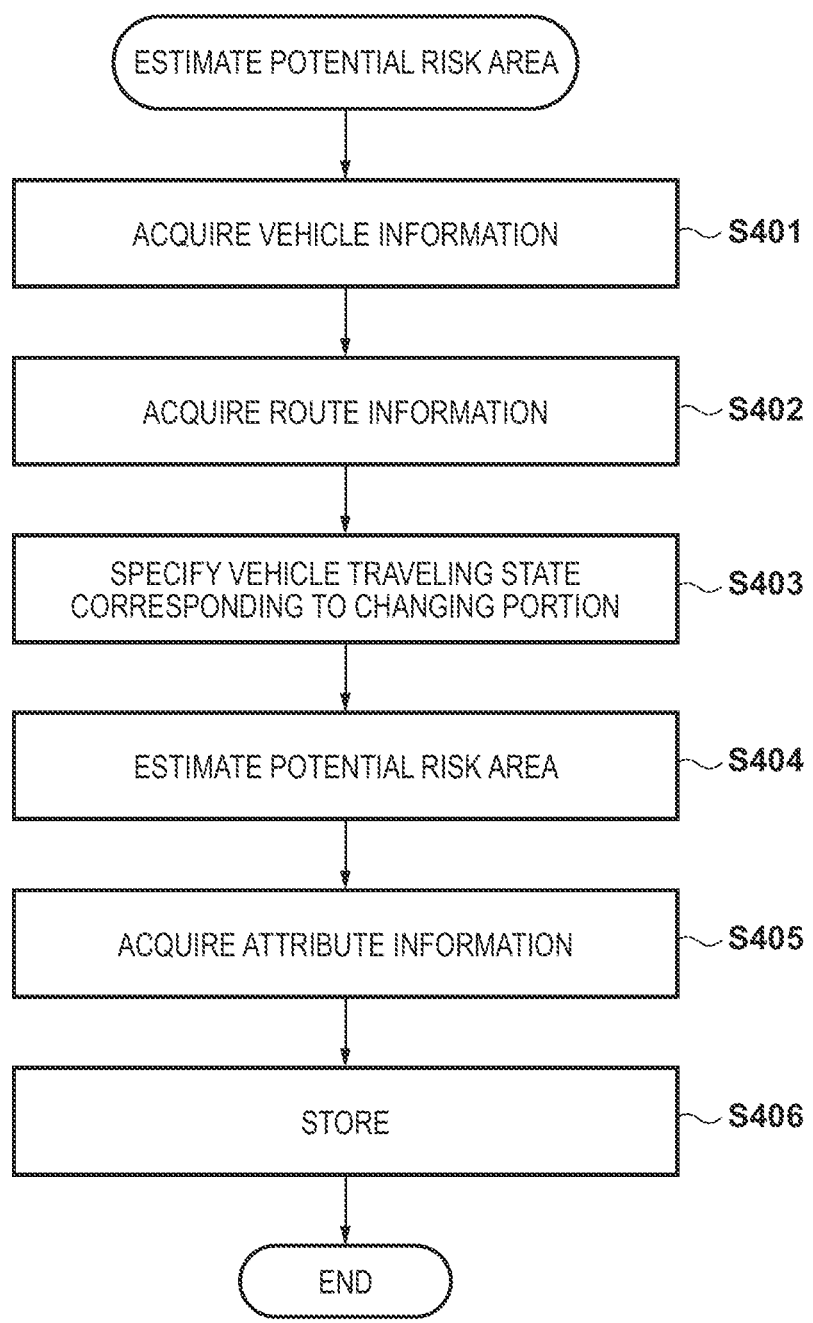
FIG. 9 is a flowchart illustrating processing for estimating a potential risk area in step S103.

FIG. 9 is a flowchart illustrating processing for estimating the potential risk area in step S203. In step S401, the data analyzing unit 204 acquires the vehicle information 217 from the personal database 216. Also, in step S402, the data analyzing unit 204 acquires the route information from the attribute information 220 of the personal database 216. Here, the vehicle information 217 is speed information corresponding to the time information, for example, and the route information is position information corresponding to the time information, for example. In step S403, the data analyzing unit 204 specifies the vehicle traveling state corresponding to the changing portion specified in step S303 based on the vehicle information acquired in step S401 and the route information acquired in step S402. Here, the vehicle traveling state is the position and speed/change rate in speed of the vehicle 101 at the time corresponding to the changing portion, for example.

In step S404, the data analyzing unit 204 estimates the potential risk area. As described with reference to FIG. 11, in the present embodiment, the point in time 1102 traced back by a predetermined time, 10 seconds for example, from the point in time 1101 at which the heart rate has increased is determined as the event occurrence time. The data analyzing unit 204 estimates the position of the vehicle 10 seconds before as the potential risk area based on the vehicle traveling state specified in step S403.

In step S405, the data analyzing unit 204 acquires the attribute information 220 based on the data, the map information 210, the weather information 211, the traffic information 212, the road surface information 213, and the like that are acquired by the data acquiring unit 203. For example, the data analyzing unit 204 acquires the information regarding driving of the vehicle 101, which includes a traveling date, a traveling route, and a time slot, for example, as the attribute information 220. Also, the data analyzing unit 204 acquires weather information in the vicinity of the potential risk area estimated in step S404, information regarding a construction, an event, and the like, information regarding road surface freeze, as the attribute information 220. Also, in step S406, the data analyzing unit 204 stores the potential risk area estimated in step S404 in the personal database 216 in association with the attribute information 220 acquired in step S405. The processing in FIG. 9 is ended after step S406. The information acquired as information regarding the vicinity of the estimated potential risk area is stored so as to be identifiable in the attribute information 220.

Figure 10:
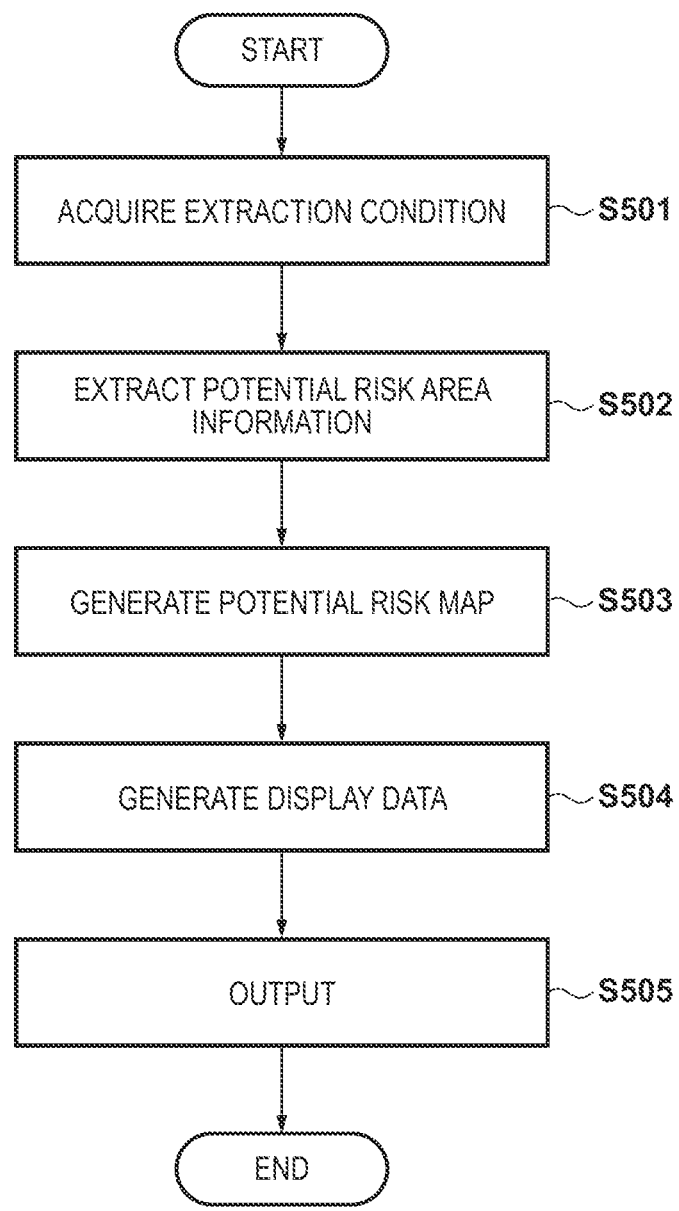
FIG. 10 is a flowchart illustrating processing until outputting of display data.

FIG. 10 is a flowchart illustrating processing in the server 109 until outputting of display data. The processing in FIG. 10 corresponds to steps S108 to S110 in FIG. 6. The processing in FIG. 10 is realized by the processor 201 executing a program that is loaded to the memory 202, for example.

In step S501, the potential risk map generating unit 205 acquires an extraction condition. The potential risk map generating unit 205 acquires the extraction condition that has been transmitted when display data is requested from the terminal 103 in step S107 in FIG. 6, for example. The extraction condition is information stored as the attribute information 220, and include a date, a time slot, route information, traffic information, road surface information, and heart rate information.

In step S502, the potential risk map generating unit 205 specifies a personal database in which the attribute information 220 corresponding to the extraction condition acquired in step S501 is stored, and extracts the potential risk area information 219 stored in the personal database. In step S503, the potential risk map generating unit 205 generates a potential risk map using the potential risk area information 219 extracted in step S502. As described already, the potential risk area information 219 is position information. The potential risk map generating unit 205 generates a map in which the location indicated by the potential risk area information 219 extracted in step S502 can be identified, based on the map information 210. For example, a map is generated in which the location indicated by the potential risk area information 219 is enclosed by a circle.

In step S504, the potential risk map generating unit 205 generates display data for display in the terminal 103 based on the potential risk map generated in step S503. The potential risk map generating unit 205 generates message data corresponding to the location indicated by the potential risk area information 219 by referring to the attribute information 220 corresponding to the potential risk area information 219. The message data is data for providing, to the user, information regarding the location indicated by the potential risk area information 219 such as "road surface is frozen" and "possible low visibility due to dense fog", for example. The potential risk map generating unit 205 links the potential risk area and the message data to each other such that when a potential risk area on the potential risk map displayed on the screen is selected (designated), the corresponding message is displayed.

In step S505, the potential risk map generating unit 205 transmits the display data generated in step S504 to the terminal 103, and ends the processing in FIG. 10. After the processing in step S505, the terminal 103 displays the potential risk map in the display unit 505 based on the received display data. Thereafter, the processing in FIG. 10 is ended.

Figure 12:
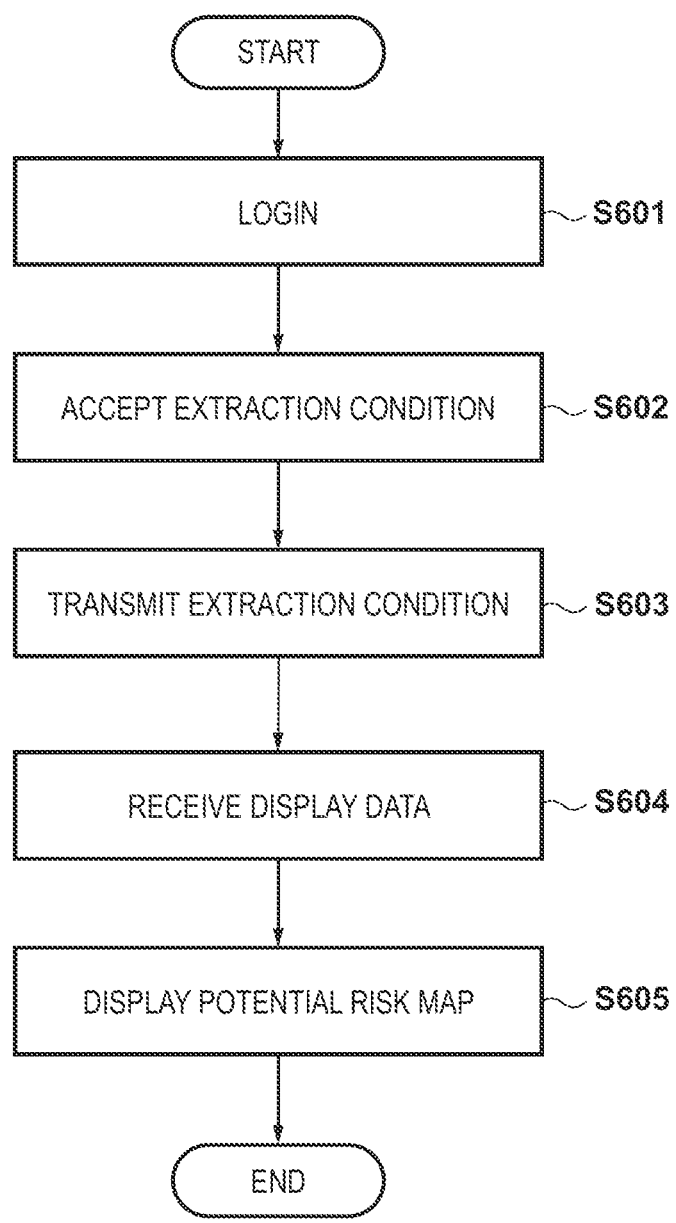
FIG. 12 is a flowchart illustrating processing until displaying display data in the terminal.

FIG. 12 is a flowchart illustrating processing until displaying of display data in the terminal 103. The processing in FIG. 12 corresponds to steps S107 and S111 in FIG. 6. The processing in FIG. 12 is realized by the processor 501 executing a program that is loaded to the memory 502, for example. The processing in FIG. 12 is started when an application that is provided by the server 109 and is for displaying the potential risk map is activated by the user A.

Figure 14:
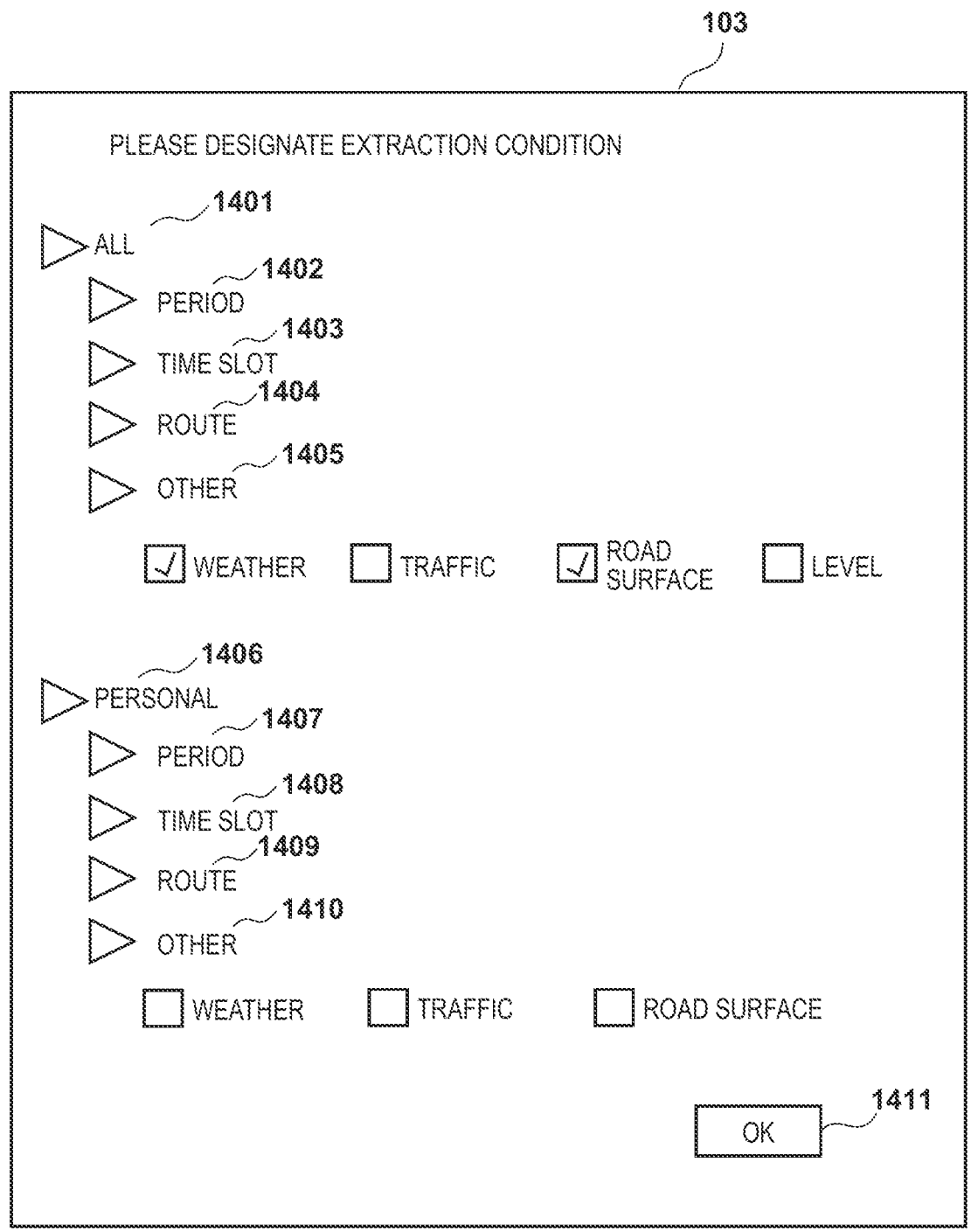
FIG. 14 is a diagram illustrating a screen for accepting designation of an extraction condition.

In step S601, the processor 501 accepts a login operation from the user A. In step S602, the processor 501 accepts designation of the extraction condition made by the user. FIG. 14 is a diagram illustrating an example of the screen for accepting designation of the extraction condition from the user. The screen in FIG. 14 is displayed when a setting menu of the extraction condition is selected from the main screen of the application after login, for example. An item 1401 is selected when displaying the potential risk map based on all of the personal databases constructed in the personal database 215 of the server 109. That is, in the display of the potential risk map, the personal databases of other users are referred to, in addition to the own personal database of the user A.

An item 1401 is selected when the user A designates a period. When the item 1401 is selected, a display area is displayed such that the period can be designated by month/date/year such as "from MM/DD/YY to MM/DD/YY". Also, an item 1403 is selected when the user designates a time slot. When the item 1403 is selected, a display area is displayed such that hour/minutes can be designated such as "hh/mm". Also, an item 1404 is selected when the user designates the route. When the item 1404 is selected, a display area is displayed such that the departure place and the arrival place can be designated. Also, an item 1405 is selected when the user A designates other conditions. The other conditions are conditions corresponding to the attribute information 220, for example. When the item 1405 is selected, selection items such as "weather", "traffic", "road surface", and "level" are displayed so as to be checked, as shown in FIG. 14, for example. For example, a user selects "weather" when the user desires to display the potential risk map considering the information regarding weather such as setting sun and snow coverage. Also, the user selects "traffic" when the user desires to display the potential risk map considering the information regarding traffic such as a construction and an event, for example. Also, the user selects "road surface" when the user desires to display the potential risk map considering the information regarding the road surface such as a fallen object, water coverage, and freezing, for example. Also, the user selects "level" when the user desires to display the potential risk map in which an occupant whose average value of the heart rate is almost the same as that of the user is targeted, or when the user desires to display the potential risk map in which an occupant whose average value is higher/lower than that of the user is targeted, for example.

The items 1402 to 1405 are not limited to the types shown in FIG. 14, and items of other types may be displayed. Also, a configuration may be adopted in which, with respect to each selection item of the item 1405 as well, when the selection item is selected, a display area is displayed using a radio button or the like such that a detailed item desired by the user can be designated as described above. For example, detailed items such as "fine weather", "rain", and "snow" may further be displayed as the detailed information regarding "weather". Also, detailed items such as "higher level", "lower level", and "same level" may further be displayed regarding "level", for example.

An item 1406 is selected when displaying the potential risk map based on the user's personal database constructed in the personal database 215 of the server 109. That is, when the potential risk map is displayed, only the own personal database of the user A is referred to. The descriptions of the items 1402, 1403, and 1404 can respectively be applied to items 1407, 1408, and 1409. Also, an item 1410 differs from the item 1405 in that the selection item "level" is not present, but the description of the item 1405 can be applied to the item 1410 regarding other points.

When a button 1411 is pressed, in step S603 in FIG. 12, the processor 501 determines the contents designated by items 1401 to 1410, and transmits the contents to the server 109 along with the identification information of the terminal 103. In step S603, when the contents of the extraction condition are transmitted to the server 109, the server 109 executes the processing in FIG. 10.

In step S505 in FIG. 10, when display data is transmitted, in step S604 in FIG. 12, the processor 501 receives the display data. Then, in step S605, the processor 501 displays the potential risk map in the display unit 505 based on the received display data. After step S605, the processing in FIG. 12 is ended.

When an extraction condition is transmitted from the terminal 103 in step S501 in FIG. 10, the server 109 specifies the corresponding personal database based on the extraction condition. For example, if the extraction condition transmitted from the terminal 103 is "road surface", a personal database is specified that includes, in the attribute information 220, information acquired from the road surface information 213 as the information in the vicinity of the potential risk area. For example, a personal database A that includes freeze information in the vicinity of a potential risk area a in the attribute information 220 and a personal database B that includes subsidence information in the vicinity of a potential risk area b in the attribute information 220 are specified.

Also, if the extraction condition transmitted from the terminal 103 is "traffic" and "road surface", for example, a personal database is specified that includes, in the attribute information 220, pieces of information respectively acquired from the traffic information 212 and road surface information 213 as the information in the vicinity of the potential risk area. For example, a personal database C that includes event information (construction is undergoing, or the like) in the vicinity of a potential risk area c in the attribute information 220 and a personal database D that includes water coverage information in the vicinity of a potential risk area d in the attribute information 220 are specified. Also, detailed information can be set in the items 1405 and 1410 in FIG. 14, for example, and when "snow" is further specified in "weather" as the detailed item, a personal database that includes weather information "snow" in the attribute information 220 is specified.

In this way, the selection items such as "weather", "traffic", "road surface", and "level" that are shown in the item 1405 in FIG. 14 may be associated with the types of database information that is retained by the server 109 in the storage unit 209, and from which the attribute information is acquired.

Figure 15:
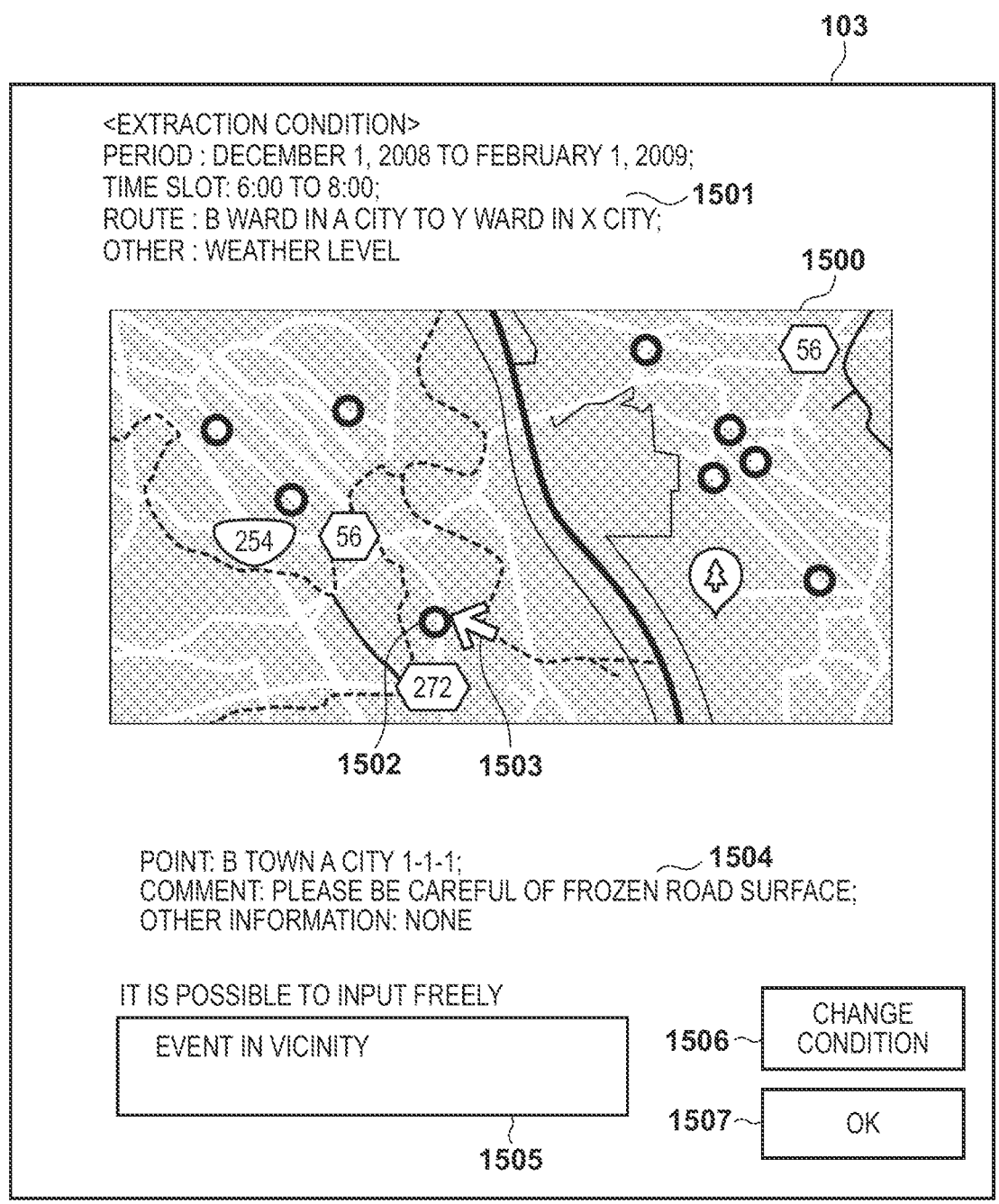
FIG. 15 is a diagram illustrating a displayed potential risk map.

FIG. 15 is a diagram illustrating an example of the potential risk map displayed in the display unit 505 of the terminal 103. A potential risk map 1500, display areas 1501 and 1504, an input area 1505, buttons 1506 and 1507 are displayed in the display unit 505. Potential risk areas 1502 indicated by circles are displayed in the potential risk map 1500. The potential risk areas 1502 are each displayed at a location corresponding to the potential risk area information 219 extracted in step S502 in FIG. 10. The extraction condition acquired in step S501 is displayed in the display area 1501. For example, in FIG. 15, a potential risk map is displayed that is generated based on the personal database 215 on the condition of the date being from Dec. 1, 2008 to Feb. 1, 2009, the time slot being 6:00 to 8:00, the area being an area including the route from B Ward in A City to Y Ward in X City, the weather (e.g., snow), and the average heart rate being the same level, for example.

A pointer 1503 can be moved by the user A, and when one potential risk area 1502 is designated, corresponding information (message) is displayed in the display area 1504. In the display area 1504, the location designated by the pointer 1503 and the message regarding the location are displayed. The message is displayed based on message data generated in step S504.

The input area 1505 is an area in which the user A can input any comment. For example, a comment such as "Event is to be held in the vicinity" is input with respect to the potential risk area 1502, as shown in FIG. 15. When a comment is input in the input area 1505 and the button 1507 is pressed by the user A, the input comment information is transmitted to the server 109 along with the identification information of the terminal 103 and the information regarding the potential risk area 1502. When the button 1506 is pressed, the screen in FIG. 14 is again displayed, and the user can change the extraction condition.

Figure 13:
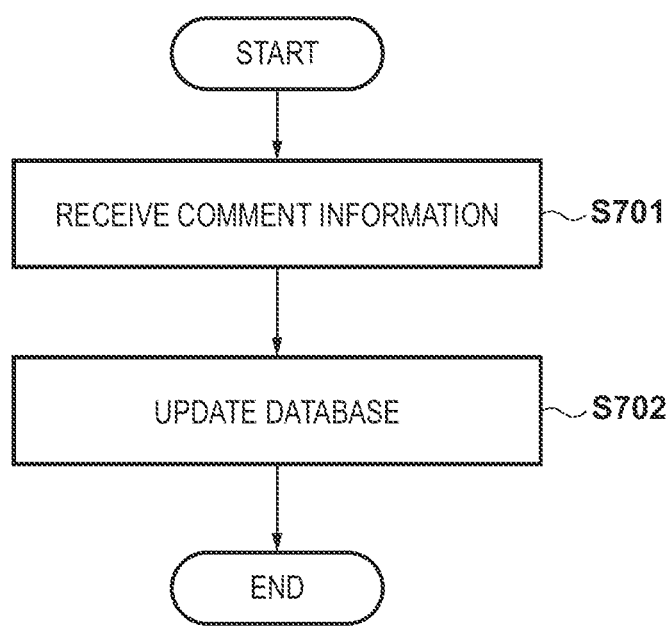
FIG. 13 is a flowchart illustrating processing in the server when comment information is transmitted.

FIG. 13 is a flowchart illustrating processing to be executed in the server 109 when the comment information input to the input area 1505 is transmitted. The processing in FIG. 13 is realized by the processor 201 executing a program that is loaded to the memory 202. In step S701, the potential risk map generating unit 205 receives comment information transmitted from the terminal 103 via the communication I/F 206. The potential risk map generating unit 205 specifies a personal database that stores the potential risk area information 219 that is the extraction target in step S502 in FIG. 10 based on the identification information of the terminal 103 and the information regarding the potential risk area 1502 that have been received along with the comment information.

Then, in step S702, the processor 201 updates the attribute information 220 of the specified personal database using the comment information received in step S701. The updating may be performed by accumulating the comment information in a predetermined storage area of the attribute information 220, or by updating the weather information, traffic information, road surface information, and the like of the attribute information 220 using the result obtained by performing word extraction on the comment information, for example. After step S702, the processing in FIG. 13 is ended.

According to the configuration described above, when the processing is in FIG. 10 is executed next time, the comment information is newly referred to in step S504. The potential risk map generating unit 205 refers to the comment information, and generates message data to be displayed in the item "other information" in the display area 1504. For example, if comment information such as "Event is to be held in the vicinity" is input and stored in the attribute information 220, the potential risk map generating unit 205 generates message data such as "Maybe crowded with people due to event" based on the comment information, as shown in a display area 1601 in FIG. 16. Such generation of the message data may be performed by statical generation based on the extracted word, or by dynamically generating a phrase by combining another attribute information such as weather. According to such a configuration, the personal database 215 in the server 109 can be updated when the user provides information, and the information provided by one user can be widely expanded to other users.

In FIG. 14, the fact that it is possible to designate that an occupant having a heart rate level that is the same as or different to that of the user is targeted has been described. For example, it is conceivable that, if the occupant A is a beginner in terms of driving of the vehicle 101, the heart rate level, e.g., an average value at the time of driving is relatively high. On the other hand, it is conceivable that the average value of heart rate, at the time of driving, of the occupant B who is an experienced driver is relatively low. It is conceivable that the number of times that the heart rate increases as a result of feeling a chill at the time of driving differs between such occupant A and occupant B. For example, the number of potential risk areas for the occupant A who is a beginner is larger than the number of potential risk area for the occupant B who is an experienced driver.

It is assumed that the potential risk map in FIG. 15 is displayed such that an occupant having a heart rate level similar to that of the occupant B who is an experienced driver is targeted. When the occupant B presses the button 1506 in order to change the extraction condition such that an occupant having a higher heart rate level than the occupant B is targeted, the displayed potential risk map is changed to that shown in FIG. 16, for example. According to such a configuration, an opportunity of paying attention to other vehicles, such as keeping a sufficient following distance, can be given to the occupant B who is an experienced driver when traveling a location that is not felt as a potential risk area by the occupant B, and as a result, the number of potential risk areas can be reduced. Also, the difference in the number of potential risk areas between FIG. 15 and FIG. 16 similarly occurs when the user itself is targeted. For example, when a certain one month five years ago is designated in the item 1407 in the FIG. 14, the potential risk map is displayed as in FIG. 16, but when a period from one month before to the current time is designated, the potential risk map is shown as in FIG. 15. As a result of displaying the potential risk map, the occupant can be forced to be cautious when traveling the locations displayed in the potential risk map, and as a result, the number of potential risk areas can be reduced with respect to the same occupant.

Also, the number of potential risk areas to be displayed may be changed by changing a specific extraction condition, out of the items 1402 to 1405. For example, when "snow" is designated as a detailed item in "weather" of the item 1405, it is highly possible that the number of potential risk areas to be displayed is increased relative to the case when "fine weather" is designated. According to such a configuration, the change in the potential risk area can be displayed by focusing on a specific condition.

Figure 16:
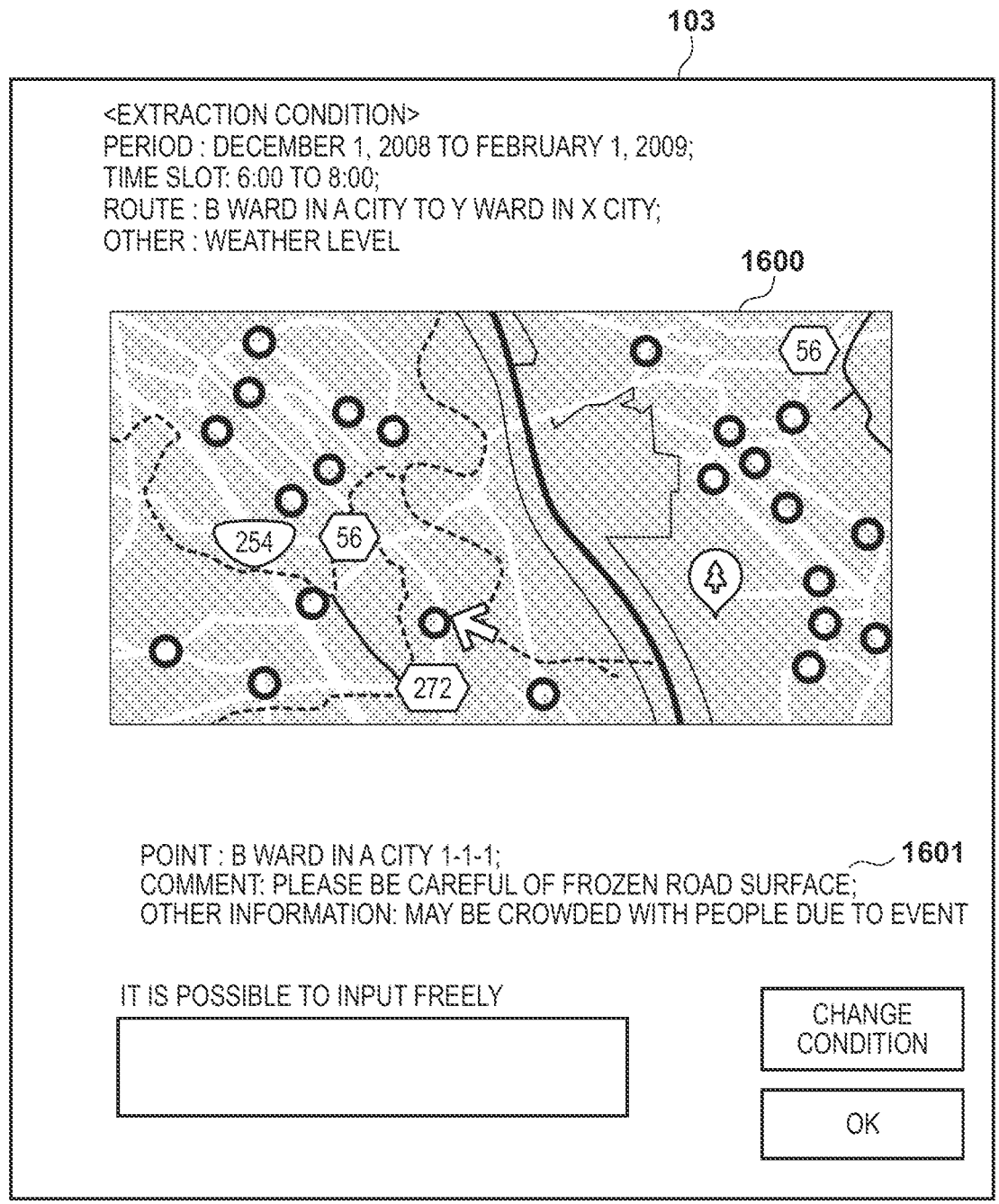
FIG. 16 is a diagram illustrating a displayed potential risk map.

In FIGS. 15 and 16, the potential risk areas are indicated by circles, but the display mode is not limited thereto, as long as the distribution of the potential risk areas can be identifiably displayed. For example, the change in distribution of the potential risk areas may be made identifiable using colors. Also, the periods 1402 and 1407 in FIG. 14 are not limited to periods until the current time, and may be future periods. For example, even in a period from the current time to one week after as well, the potential risk area information may be extracted based on weather forecast information included in the weather information 211.

Also, in the present embodiment, the point in time 1102 traced back by a predetermined time, 10 seconds for example, from the point in time 1101 at which the heart rate has increased is determined as the event occurrence time, but the predetermined time may also be able to be set in the server 109.

Also, the configuration may be such that the correction information regarding each respective displayed potential risk area can be collected in the server 109 using the input area 1505 or the like, and the aforementioned predetermined time is corrected for each potential risk area based on the correction information. For example, a configuration may be adopted in which a selection item such as "need correction" is provided in combination with the input area 1505, and the position correction made by moving the potential risk area 1502 on the potential risk map 1500 is accepted. The server 109 may also be configured to receive such correction information in step S701, and the predetermined time of aforementioned 10 seconds is corrected regarding the potential risk area by an amount corresponding to the received correction information amount. For example, if a potential risk area estimated using the predetermined time of 10 seconds is corrected regarding the position thereof by many users, the server 109 makes correction from 10 seconds to 8 seconds with respect to the potential risk area. This is a case where, if the corrected position is a location at which anxiety is particularly prompted such as a risk that a large rock will drop being present in actuality, the heart rate is considered to increase in a shorter period of time. As a result of correction based on such correction information, a more suitable potential risk map can be provided.

Summary of Embodiment

The information providing system of the embodiment described above is an information providing system (100) including a vehicle (101) and a server (109), wherein the server includes an acquiring unit (step S201) for acquiring heart rate data of an occupant of the vehicle acquired by a wearable terminal attached to the occupant, and an estimating unit configured to estimate a potential risk area that is a cause to increase a heart rate based on the heart rate data acquired by the acquiring unit (step S203), and the estimating unit specifies a point in time a predetermined time before a point in time at which the heart rate indicated by the heart rate data increases, and estimates the position of the vehicle corresponding to the specified point in time as the potential risk area (1102). According to such a configuration, a point in time a predetermined time before a point in time at which the heart rate increases is specified, and the position of the vehicle corresponding to the specified point in time can be estimated as the potential risk area.

Also, the information providing system further includes a generating unit configured to generate a potential risk map in which the potential risk area estimated by the estimating unit is identifiably displayed (step S503). According to such a configuration, a potential risk map in which the estimated potential risk area is identifiably displayed can be generated.

Also, the vehicle further includes first transmitting unit configured to transmit vehicle information to the server (step S102), and the estimating unit estimates the potential risk area based on the vehicle information corresponding to the specified point in time out of the vehicle information transmitted by the first transmitting unit. According to such a configuration, the vehicle information corresponding to a point in time a predetermined time before a point in time at which the heart rate increases need only be used, and therefore the processing load can be reduced.

Also, the vehicle information includes information regarding speed and a position of the vehicle. According to such a configuration, speed and position information of a vehicle can be used as the vehicle information.

Also, the estimating unit estimates the point in time a predetermined time before, from the point in time at which the heart rate has exceeded a threshold value at a predetermined increase rate. According to such a configuration, the point in time a predetermined time before the point in time at which the heart rate has exceeded a threshold value at a predetermined increase rate can be estimated as the potential risk area.

Also, the information providing system further includes a display terminal (103), and the server further includes a second transmitting unit configured to transmit display data for displaying the potential risk map generated by the generating unit to the display terminal (step S505). Also, the display terminal includes a display unit configured to display the potential risk map based on the display data transmitted by the second transmitting unit (step S605). According to such a configuration, the potential risk map can be displayed in the display terminal.

Also, the display terminal further includes an accepting unit configured to accept a condition for displaying the potential risk map (step S602), and a third transmitting unit configured to transmit the condition accepted by the accepting unit to the server (step S603), and the generating unit generates the potential risk map in accordance with the condition transmitted by the third transmitting unit. According to such a configuration, the potential risk map in accordance with the condition can be generated.

Also, the server further includes storing unit (214) for storing the potential risk area estimated by the estimating unit and attribute information so as to be associated with each other, and the generating unit generates the potential risk map based on the potential risk area associated with the attribute information that satisfies the condition. According to such a configuration, the attribute information can be used as the condition for generating the potential risk map.

Also, the attribute information includes at least any of a date, a time slot, and route information. Also, the attribute information includes at least any of weather information, traffic information, road surface information, and heart rate information. According to such a configuration, a date, a time slot, route information, weather information, traffic information, road surface information, and heart rate information can be used as the attribute information.

Also, the display terminal further includes a second accepting unit (1505) configured to accept a comment after the potential risk map is displayed by the display unit, and a fourth transmitting unit (1507) configured to transmit the comment accepted by the second accepting unit to the server, and the server further includes an updating unit configured to update the attribute information based on the comment transmitted by the fourth transmitting unit (step S702). According to such a configuration, the attribute information can be updated based on the comment accepted by the display terminal.

Also, an uploading unit configured to upload the heart rate data to the server (step S104) is further included, and the acquiring unit acquires the heart rate data uploaded by the uploading unit. According to such a configuration, uploaded heart rate data can be acquired.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An information providing system including a vehicle and a server, the information providing system comprising:
    an accepting unit configured to accept a reference heart rate level as a condition for displaying a risk map;
    an acquiring unit configured to acquire heart rate data of an occupant of the vehicle acquired by a wearable terminal attached to the occupant;
    a storing unit configured to store the heart rate data acquired by the acquiring unit;
    a specifying unit configured to specify a traveling state of the vehicle corresponding to a changing portion in which the amount of change in heart rate indicated by the heart rate data that satisfies the reference level accepted by the accepting unit, out of the heart rate data stored in the storing unit, is larger than a threshold value;
    an estimating unit configured to estimate the position of the vehicle at a point in time traced back by a predetermined time from the time corresponding to the changing portion as a risk area in which an event that causes the change in heart rate has occurred, based on the traveling state of the vehicle specified by the specifying unit, and
    a generating unit configured to generate the risk map in which the risk area estimated by the estimating unit is identifiably displayed,
    wherein the server includes the acquiring unit, the storing unit, the specifying unit, the estimating unit, and the generating unit.

2. The information providing system according to claim 1, wherein
    the vehicle further includes a first transmitting unit configured to transmit vehicle information to the server, and
    the estimating unit estimates the risk area based on the vehicle information corresponding to a point in time traced by a predetermined time from the time corresponding to the changing portion, out of the vehicle information transmitted by the first transmitting unit.

3. The information providing system according to claim 2, wherein
    the vehicle information includes information regarding speed and a position of the vehicle.

4. The information providing system according to claim 1, further comprising
    a display terminal,
    wherein the server further includes a second transmitting unit configured to transmit display data for displaying the risk map generated by the generating unit to the display terminal.

5. The information providing system according to claim 4, wherein
    the display terminal includes a display unit configured to display the risk map based on the display data transmitted by the second transmitting unit.

6. The information providing system according to claim 5, wherein
    the display terminal further includes
    the accepting unit, and
    a third transmitting unit configured to transmit the condition accepted by the accepting unit to the server, and
    the generating unit generates the risk map in accordance with the condition transmitted by the third transmitting unit.

7. The information providing system according to claim 6, wherein
    the storing unit further stores the risk area estimated by the estimating unit and attribute information so as to be associated with each other, and
    the generating unit generates the risk map based on the risk area associated with the attribute information that satisfies the condition.

8. The information providing system according to claim 7, wherein
    the attribute information includes at least any of a date, a time slot, and route information.

9. The information providing system according to claim 7, wherein the attribute information includes at least any of weather information, traffic information, road surface information, and heart rate information.

10. The information providing system according to claim 7, wherein
the display terminal further includes
a second accepting unit configured to accept information after the risk map is displayed by the display unit, and
a fourth transmitting unit configured to transmit the information accepted by the second accepting unit to the server, and
the server further includes an updating unit configured to update the attribute information based on the information transmitted by the fourth transmitting unit.

11. The information providing system according to claim 1, further comprising
an uploading unit configured to upload the heart rate data to the server,
wherein the acquiring unit acquires the heart rate data uploaded by the uploading unit.

12. A method to be executed in an information providing system including a vehicle and a server, the method comprising:
an accepting step of accepting a reference heart rate level as a condition for displaying a risk map,
an acquiring step of the server acquiring heart rate data of an occupant of the vehicle acquired by a wearable terminal attached to the occupant, and
a storing step of the server storing the heart rate data acquired in the acquiring step,
a specifying step of the server specifying a traveling state of the vehicle corresponding to a changing portion in which the amount of change in heart rate indicated by the heart rate data that satisfies the reference level accepted in the accepting step, out of the heart rate data stored in the storing step, is larger than a threshold value,
an estimating step of the server estimating the position of the vehicle at a point in time traced back by a predetermined time from the time corresponding to the changing portion as a risk area in which an event that causes the change in heart rate has occurred, based on the traveling state of the vehicle specified in the specifying step, and
a generating step of the server generating the risk map in which the risk area estimated in the estimating step is identifiably displayed.

13. A server comprising:
an acquiring unit configured to acquire heart rate data of an occupant of a vehicle;
a storing unit configured to store the heart rate data acquired by the acquiring unit;
a specifying unit configured to specify a traveling state of the vehicle corresponding to a changing portion in which the amount of change in heart rate is larger than a threshold value, the heart rate being indicated by heart rate data that satisfies a reference level accepted by accepting unit for accepting the reference level of the heart rate, as a condition for displaying a risk map, out of the heart rate data stored in the storing unit;
an estimating unit configured to estimate the position of the vehicle at a point in time traced back by a predetermined time from the time corresponding to the changing portion as a risk area in which an event that causes the change in heart rate has occurred, based on the traveling state of the vehicle specified by the specifying unit; and
a generating unit configured to generate the risk map in which the risk area estimated by the estimating unit is identifiably displayed.

14. A method to be executed in a server, the method comprising:
an accepting step of accepting a reference heart rate level as a condition for displaying a risk map;
an acquiring step of acquiring heart rate data of an occupant of a vehicle;
a storing step of storing the heart rate data acquired in the acquiring step;
a specifying step of specifying a traveling state of the vehicle corresponding to a changing portion in which the amount of change in heart rate is larger than a threshold value, the heart rate being indicated by heart rate data that satisfies the reference level accepted by the accepting step, out of the heart rate data stored in the storing step;
an estimating step of estimating the position of the vehicle at a point in time traced back by a predetermined time from the time corresponding to the changing portion as a risk area in which an event that causes the change in heart rate has occurred, based on the traveling state of the vehicle specified in the specifying step; and
a generating step of generating the risk map in which the risk area estimated in the estimating step is identifiably displayed.

15. A non-transitory computer-readable storage medium storing a program causing a computer to function as:
an acquiring unit configured to acquire heart rate data of an occupant of a vehicle;
a storing unit configured to store the heart rate data acquired by the acquiring unit;
a specifying unit configured to specify a traveling state of the vehicle corresponding to a changing portion in which the amount of change in heart rate is larger than a threshold value, the heart rate being indicated by heart rate data that satisfies a reference level accepted by an accepting unit configured to accept the reference level of the heart rate, as a condition for displaying a risk map, out of the heart rate data stored in the storing unit;
an estimating unit configured to estimate the position of the vehicle at a point in time traced back by a predetermined time from the time corresponding to the changing portion as a risk area in which an event that causes the change in heart rate has occurred, based on the traveling state of the vehicle specified by the specifying unit; and
a generating unit configured to generate the risk map in which the risk area estimated by the estimating unit is identifiably displayed.

* * * * *